United States Patent
Li et al.

(10) Patent No.: US 12,247,081 B2
(45) Date of Patent: *Mar. 11, 2025

(54) CEACAM5-DEPENDENT 4-1BB-AGONISTIC BISPECIFIC ANTIBODIES

(71) Applicant: LANOVA MEDICINES LIMITED, Shanghai (CN)

(72) Inventors: Runsheng Li, Shanghai (CN); Wei Cao, Shanghai (CN); Ying Qin Zang, Shanghai (CN); Wentao Huang, Shanghai (CN)

(73) Assignee: LANOVA MEDICINES LIMITED, Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/658,896

(22) Filed: May 8, 2024

(65) Prior Publication Data
US 2024/0294656 A1    Sep. 5, 2024

Related U.S. Application Data

(63) Continuation of application No. PCT/CN2024/078991, filed on Feb. 28, 2024.

(51) Int. Cl.
| C07K 16/28 | (2006.01) |
| A61K 39/00 | (2006.01) |
| A61P 35/00 | (2006.01) |
| C07K 16/30 | (2006.01) |

(52) U.S. Cl.
CPC .......... *C07K 16/2878* (2013.01); *A61P 35/00* (2018.01); *C07K 16/3007* (2013.01); *A61K 2039/505* (2013.01); *C07K 2317/22* (2013.01); *C07K 2317/24* (2013.01); *C07K 2317/31* (2013.01); *C07K 2317/33* (2013.01); *C07K 2317/52* (2013.01); *C07K 2317/569* (2013.01); *C07K 2317/73* (2013.01); *C07K 2317/92* (2013.01)

(58) Field of Classification Search
None
See application file for complete search history.

(56) References Cited

U.S. PATENT DOCUMENTS

2018/0021440 A1    1/2018    Yu et al.

FOREIGN PATENT DOCUMENTS

| CN | 108659131 A | 10/2018 | |
| WO | 2010001251 A2 | 1/2010 | |
| WO | 2016165302 A1 | 10/2016 | |
| WO | 2022242679 A1 | 11/2022 | |
| WO | WO-2023030258 A1 * | 3/2023 | .............. A61P 35/00 |

OTHER PUBLICATIONS

Powell et al. A functional genomic screen in vivo identifies CEACAM5 as a clinically relevant driver of breast cancer metastasis. npj Breast Cancer, 2018; 4(9):1-12. (Year: 2018).*
International Search Report for PCT International Application No. PCT/CN2024/078991, dated Jun. 3, 2024, 6 pages.
Written Opinion of the International Searching Authority for PCT International Application No. PCT/CN2024/078991, dated Jun. 3, 2024, 4 pages.
Decary, S. et al. "Preclinical Activity of SAR408701: A Novel Anti-CEACAM5-maytansinoid Antibody-drug Conjugate for the Treatment of CEACAM5-positive Epithelial Tumors" Clinical Cancer Research, vol. 26, No. 24, Dec. 15, 2020 (Dec. 15, 2020), pp. 6589-6599.
Muik, A. et al. "Preclinical Characterization and Phase I Trial Results of a Bispecific Antibody Targeting PD-L1 and 4-1BB (GEN1046) in Patients with Advanced Refractory Solid Tumors" Cancer Discovery, Feb. 17, 2022 (Feb. 17, 2022), pp. 1248-1265.

* cited by examiner

*Primary Examiner* — Daniel E Kolker
*Assistant Examiner* — Maureen Varina Driscoll
(74) *Attorney, Agent, or Firm* — Sheppard, Mullin, Richter & Hampton LLP

(57) ABSTRACT

Provided are bispecific or multispecific antibodies that include an anti-CEACAM5 portion and one or more anti-4-1BB nanobodies whose agonist activity is dependent on the presence of the CEACAM5 antigen. Such bispecific or multispecific antibodies are safe, and are efficacious in treating cancer and have long-term protective immunological memory against tumors. Methods of using the antibodies for treating diseases such as cancer are also provided.

18 Claims, 13 Drawing Sheets
Specification includes a Sequence Listing.

SEQUENCE LISTING

```
Sequence total quantity: 39
SEQ ID NO: 1            moltype = AA  length = 122
FEATURE                 Location/Qualifiers
source                  1..122
                        mol_type = protein
                        organism = Lama glama
SEQUENCE: 1
EVQLVESGGG LVQPGGSLRL SCAASGFTFS SSAMSWARQT PGKGFEWVSG IYSDGSTYYT  60
DSVKDRFTIS RDNAKNTVYL QMNSLKPEDT AVYYCATWGT LRFGVWAEYD HWGQGTQVTV  120
SS                                                                122

SEQ ID NO: 2            moltype = AA  length = 122
FEATURE                 Location/Qualifiers
source                  1..122
                        mol_type = protein
                        organism = unidentified
SEQUENCE: 2
EVQLLESGGG LVQPGGSLRL SCAASGFTFS SSAMSWARQA PGKGLEWVSG IYSGGSTYYT  60
ESVKDRFTIS RDNSKNTLYL QMNSLRAEDT AVYYCAKWGT LRFGVWAEYD HWGQGTLVTV  120
SS                                                                122

SEQ ID NO: 3            moltype = AA  length = 122
FEATURE                 Location/Qualifiers
source                  1..122
                        mol_type = protein
                        organism = synthetic construct
SEQUENCE: 3
EVQLLESGGG LVQPGGSLRL SCAASGFTFS SSAMSWARQA PGKGLEWVSG IYSGGSTYYT  60
ESVKDRFTIS RDNSKNTVYL QMNSLKPEDT AVYYCATWGT LRFGVWAEYD HWGQGTLVTV  120
SS                                                                122

SEQ ID NO: 4            moltype = AA  length = 122
FEATURE                 Location/Qualifiers
source                  1..122
                        mol_type = protein
                        organism = synthetic construct
SEQUENCE: 4
EVQLLESGGG LVQPGGSLRL SCAASGFTFS SSAMSWARQT PGKGFEWVSG IYSGGSTYYT  60
ESVKDRFTIS RDNSKNTVYL QMNSLKPEDT AVYYCATWGT LRFGVWAEYD HWGQGTQVTV  120
SS                                                                122
```

```
SEQ ID NO: 5              moltype = AA   length = 122
FEATURE                   Location/Qualifiers
source                    1..122
                          mol_type = protein
                          organism = synthetic construct
SEQUENCE: 5
EVQLLESGGG LVQPGGSLRL SCAASGFTFS SSAMSWARQA PGKGFEWVSG IYSGGSTYYT    60
ESVKDRFTIS RDNSKNTLYL QMNSLRAEDT AVYYCAKWGT LRFGVWAEYD HWGQGTLVTV   120
SS                                                                  122

SEQ ID NO: 6              moltype = AA   length = 122
FEATURE                   Location/Qualifiers
source                    1..122
                          mol_type = protein
                          organism = synthetic construct
SEQUENCE: 6
EVQLVESGGG LVQPGGSLRL SCAASGFTFS SSAMSWARQA PGKGLEWVSG IYSGGSTYYT    60
ESVKDRFTIS RDNAKNTLYL QMNSLRPEDT AVYYCATWGT LRFGVWAEYD HWGQGTLVTV   120
SS                                                                  122

SEQ ID NO: 7              moltype = AA   length = 122
FEATURE                   Location/Qualifiers
source                    1..122
                          mol_type = protein
                          organism = synthetic construct
SEQUENCE: 7
EVQLVESGGG LVQPGGSLRL SCAASGFTFS SSAMSWARQA PGKGFEWVSG IYSGGSTYYT    60
ESVKDRFTIS RDNAKNTVYL QMNSLKPEDT AVYYCATWGT LRFGVWAEYD HWGQGTLVTV   120
SS                                                                  122

SEQ ID NO: 8              moltype = AA   length = 122
FEATURE                   Location/Qualifiers
source                    1..122
                          mol_type = protein
                          organism = synthetic construct
SEQUENCE: 8
QVQLVESGGG LVKPGGSLRL SCAASGFTFS SSAMSWARQA PGKGLEWVSG IYSGGSTYYT    60
ESVKDRFTIS RDNAKNSLYL QMNSLRAEDT AVYYCARWGT LRFGVWAEYD HWGQGTLVTV   120
SS                                                                  122

SEQ ID NO: 9              moltype = AA   length = 122
FEATURE                   Location/Qualifiers
source                    1..122
                          mol_type = protein
                          organism = synthetic construct
SEQUENCE: 9
QVQLVESGGG LVKPGGSLRL SCAASGFTFS SSAMSWARQA PGKGFEWVSG IYSGGSTYYT    60
ESVKDRFTIS RDNAKNSLYL QMNSLRPEDT AVYYCATWGT LRFGVWAEYD HWGQGTQVTV   120
SS                                                                  122

SEQ ID NO: 10             moltype = AA   length = 122
FEATURE                   Location/Qualifiers
source                    1..122
                          mol_type = protein
                          organism = synthetic construct
SEQUENCE: 10
QVQLVESGGG LVQPGGSLRL SCAASGFTFS SSAMSWARQA PGKGFEWVSG IYSGGSTYYT    60
ESVKDRFTIS RDNAKNSVYL QMNSLKPEDT AVYYCATWGT LRFGVWAEYD HWGQGTQVTV   120
SS                                                                  122

SEQ ID NO: 11             moltype = AA   length = 122
FEATURE                   Location/Qualifiers
source                    1..122
                          mol_type = protein
                          organism = synthetic construct
SEQUENCE: 11
EVDLVESGGG LVQPGGSLRL SCAVSGFTFS NSAMSWARQA PGKEFEWVSS IYSDGKTYYV    60
DSVKGRFTIS RDNAKNTVYL QMSSLKPEDT AVYYCATWKT LRVGVWDESD YWGQGTQVTV   120
SS                                                                  122

SEQ ID NO: 12             moltype = AA   length = 122
FEATURE                   Location/Qualifiers
source                    1..122
                          mol_type = protein
                          organism = synthetic construct
```

```
SEQUENCE: 12
EVQLLESGGG  LVQPGGSLRL  SCAASGFTFS  SSAMSWARQA  PGKGLEWVSS  IYSSGKTYYV   60
ESVKGRFTIS  RDNSKNTLYL  QMNSLRAEDT  AVYYCAKWKT  LRVGVWDESD  YWGQGTLVTV  120
SS                                                                     122

SEQ ID NO: 13           moltype = AA  length = 122
FEATURE                 Location/Qualifiers
source                  1..122
                        mol_type = protein
                        organism = synthetic construct
SEQUENCE: 13
EVQLLESGGG  LVQPGGSLRL  SCAASGFTFS  SSAMSWARQA  PGKELEWVSS  IYSSGKTYYV   60
ESVKGRFTIS  RDNAKNTLYL  QMSSLRAEDT  AVYYCATWKT  LRVGVWDESD  YWGQGTLVTV  120
SS                                                                     122

SEQ ID NO: 14           moltype = AA  length = 122
FEATURE                 Location/Qualifiers
source                  1..122
                        mol_type = protein
                        organism = synthetic construct
SEQUENCE: 14
EVDLVESGGG  LVQPGGSLRL  SCAVSGFTFS  SSAMSWARQA  PGKEFEWVSS  IYSSGKTYYV   60
ESVKGRFTIS  RDNAKNTVYL  QMSSLRPEDT  AVYYCATWKT  LRVGVWDESD  YWGQGTLVTV  120
SS                                                                     122

SEQ ID NO: 15           moltype = AA  length = 122
FEATURE                 Location/Qualifiers
source                  1..122
                        mol_type = protein
                        organism = synthetic construct
SEQUENCE: 15
EVQLVESGGG  LIQPGGSLRL  SCAASGFTFS  SSAMSWARQA  PGKGFEWVSS  IYSSGKTYYV   60
ESVKGRFTIS  RDNSKNTLYL  QMNSLRAEDT  AVYYCARWKT  LRVGVWDESD  YWGQGTLVTV  120
SS                                                                     122

SEQ ID NO: 16           moltype = AA  length = 122
FEATURE                 Location/Qualifiers
source                  1..122
                        mol_type = protein
                        organism = synthetic construct
SEQUENCE: 16
EVQLVESGGG  LIQPGGSLRL  SCAASGFTFS  SSAMSWARQA  PGKEFEWVSS  IYSSGKTYYV   60
ESVKGRFTIS  RDNAKNTLYL  QMSSLRAEDT  AVYYCATWKT  LRVGVWDESD  YWGQGTQVTV  120
SS                                                                     122

SEQ ID NO: 17           moltype = AA  length = 122
FEATURE                 Location/Qualifiers
source                  1..122
                        mol_type = protein
                        organism = synthetic construct
SEQUENCE: 17
EVQLVESGGG  LVQPGGSLRL  SCAVSGFTFS  SSAMSWARQA  PGKEFEWVSS  IYSSGKTYYV   60
ESVKGRFTIS  RDNAKNTVYL  QMSSLRPEDT  AVYYCATWKT  LRVGVWDESD  YWGQGTQVTV  120
SS                                                                     122

SEQ ID NO: 18           moltype = AA  length = 122
FEATURE                 Location/Qualifiers
source                  1..122
                        mol_type = protein
                        organism = synthetic construct
SEQUENCE: 18
EVQLVESGGG  LVQPGGSLRL  SCAASGFTFS  SSAMSWARQA  PGKGFEWVAS  IYSSGKTYYV   60
ESVKGRFTIS  RDNAKNSLYL  QMNSLRAEDT  AVYYCARWKT  LRVGVWDESD  YWGQGTLVTV  120
SS                                                                     122

SEQ ID NO: 19           moltype = AA  length = 122
FEATURE                 Location/Qualifiers
source                  1..122
                        mol_type = protein
                        organism = synthetic construct
SEQUENCE: 19
EVQLVESGGG  LVQPGGSLRL  SCAASGFTFS  SSAMSWARQA  PGKGFEWVSS  IYSSGKTYYV   60
ESVKGRFTIS  RDNAKNSLYL  QMSSLRAEDT  AVYYCATWKT  LRVGVWDESD  YWGQGTLVTV  120
SS                                                                     122

SEQ ID NO: 20           moltype = AA  length = 122
FEATURE                 Location/Qualifiers
```

```
                        source           1..122
                                         mol_type = protein
                                         organism = synthetic construct
SEQUENCE: 20
EVQLVESGGG LVQPGGSLRL SCAVSGFTFS SSAMSWARQA PGKEFEWVSS IYSSGKTYYV    60
ESVKGRFTIS RDNAKNSVYL QMSSLRPEDT AVYYCATWKT LRVGVWDESD YWGQGTLVTV   120
SS                                                                 122

SEQ ID NO: 21           moltype = AA   length = 5
FEATURE                 Location/Qualifiers
source                  1..5
                        mol_type = protein
                        organism = Lama glama
SEQUENCE: 21
SSAMS                                                                5

SEQ ID NO: 22           moltype = AA   length = 16
FEATURE                 Location/Qualifiers
source                  1..16
                        mol_type = protein
                        organism = synthetic construct
SEQUENCE: 22
GIYSGGSTYY TESVKD                                                   16

SEQ ID NO: 23           moltype = AA   length = 14
FEATURE                 Location/Qualifiers
source                  1..14
                        mol_type = protein
                        organism = Lama glama
SEQUENCE: 23
WGTLRFGVWA EYDH                                                     14

SEQ ID NO: 24           moltype = AA   length = 16
FEATURE                 Location/Qualifiers
source                  1..16
                        mol_type = protein
                        organism = Lama glama
SEQUENCE: 24
GIYSDGSTYY TDSVKD                                                   16

SEQ ID NO: 25           moltype = AA   length = 16
FEATURE                 Location/Qualifiers
source                  1..16
                        mol_type = protein
                        organism = synthetic construct
SEQUENCE: 25
SIYSSGKTYY VESVKG                                                   16

SEQ ID NO: 26           moltype = AA   length = 14
FEATURE                 Location/Qualifiers
source                  1..14
                        mol_type = protein
                        organism = synthetic construct
SEQUENCE: 26
WKTLRVGVWD ESDY                                                     14

SEQ ID NO: 27           moltype = AA   length = 5
FEATURE                 Location/Qualifiers
source                  1..5
                        mol_type = protein
                        organism = synthetic construct
SEQUENCE: 27
NSAMS                                                                5

SEQ ID NO: 28           moltype = AA   length = 16
FEATURE                 Location/Qualifiers
source                  1..16
                        mol_type = protein
                        organism = synthetic construct
SEQUENCE: 28
SIYSDGKTYY VDSVKG                                                   16

SEQ ID NO: 29           moltype = AA   length = 119
FEATURE                 Location/Qualifiers
source                  1..119
                        mol_type = protein
                        organism = synthetic construct
```

```
SEQUENCE: 29
EVQLVESGGG VVQPGRSLRL SCSASGFDFT TYWMSWVRQA PGKGLEWIGE IHPDSSTINY    60
APSLKDRFTI SRDNAKNTLF LQMDSLRPED TGVYFCASLY FGFPWFAYWG QGTPVTVSS    119

SEQ ID NO: 30             moltype = AA  length = 106
FEATURE                   Location/Qualifiers
source                    1..106
                          mol_type = protein
                          organism = synthetic construct
SEQUENCE: 30
DIQLTQSPSS LSASVGDRVT ITCKASQDVG TSVAWYQQKP GKAPKLLIYW TSTRHTGVPS    60
RFSGSGSGTD FTFTISSLQP EDIATYYCQQ YSLYRSFGQG TKVEIK                  106

SEQ ID NO: 31             moltype = AA  length = 5
FEATURE                   Location/Qualifiers
source                    1..5
                          mol_type = protein
                          organism = synthetic construct
SEQUENCE: 31
TYWMS                                                                5

SEQ ID NO: 32             moltype = AA  length = 17
FEATURE                   Location/Qualifiers
source                    1..17
                          mol_type = protein
                          organism = synthetic construct
SEQUENCE: 32
EIHPDSSTIN YAPSLKD                                                   17

SEQ ID NO: 33             moltype = AA  length = 10
FEATURE                   Location/Qualifiers
source                    1..10
                          mol_type = protein
                          organism = synthetic construct
SEQUENCE: 33
LYFGFPWFAY                                                           10

SEQ ID NO: 34             moltype = AA  length = 11
FEATURE                   Location/Qualifiers
source                    1..11
                          mol_type = protein
                          organism = synthetic construct
SEQUENCE: 34
KASQDVGTSV A                                                         11

SEQ ID NO: 35             moltype = AA  length = 7
FEATURE                   Location/Qualifiers
source                    1..7
                          mol_type = protein
                          organism = synthetic construct
SEQUENCE: 35
WTSTRHT                                                              7

SEQ ID NO: 36             moltype = AA  length = 8
FEATURE                   Location/Qualifiers
source                    1..8
                          mol_type = protein
                          organism = synthetic construct
SEQUENCE: 36
QQYSLYRS                                                             8

SEQ ID NO: 37             moltype = AA  length = 122
FEATURE                   Location/Qualifiers
source                    1..122
                          mol_type = protein
                          organism = synthetic construct
SEQUENCE: 37
EVQLVESGGG LVQPGGSLRL SCAASGFTFS SSAMSWARQA PGKGFEWVSG IYSGGSTYYT    60
ESVKDRFTIS RDNSKNTVYL QMNSLKPEDT AVYYCATWGT LRFGVWAEYD HWGQGTQVTV    120
SS                                                                   122

SEQ ID NO: 38             moltype = AA  length = 122
FEATURE                   Location/Qualifiers
source                    1..122
                          mol_type = protein
                          organism = synthetic construct
```

```
SEQUENCE: 38
EVQLVESGGG LVQPGGSLRL SCAASGFTFS SSAMSWARQA PGKGFEWVSG IYSGGSTYYT    60
ESVKDRFTIS RDNAKNTVYL QMNSLKPEDT AVYYCATWGT LRFGVWAEYD HWGQGTLVTV   120
SS                                                                 122

SEQ ID NO: 39            moltype = AA  length = 20
FEATURE                  Location/Qualifiers
source                   1..20
                         mol_type = protein
                         organism = synthetic construct
SEQUENCE: 39
GGGGSGGGGS GGGGSGGGGS                                               20
```

CEACAM5-DEPENDENT 4-1BB-AGONISTIC BISPECIFIC ANTIBODIES

CROSS REFERENCE TO RELATED APPLICATIONS

The present application is a continuation of International Application No. PCT/CN2024/078991, filed Feb. 28, 2024, which claims priority to International Application No. PCT/CN2023/078788, filed Feb. 28, 2023, the content of each of which is incorporated herein by reference in its entirety in the present disclosure.

REFERENCE TO AN ELECTRONIC SEQUENCE LISTING

The contents of the electronic sequence listing (358714.xml; Size: 37,499 bytes; and Date of Creation: Feb. 28, 2024) is herein incorporated by reference in its entirety.

BACKGROUND 4-1BB (CD137, tumor necrosis factor receptor superfamily 9) plays an important role in modulating the activity of various immune cells. 4-1BB agonists enhance immune cell proliferation, survival, secretion of cytokines and cytolytic activity CD8 T cells. Activation of 4-1BB enhances immune response to eliminate tumors in mice.

Commonly known anti-4-1BB antibodies, such as utomilumab (PF-05082566) and urelumab (BMS-663513), are agonist antibodies. These agonist antibodies are associated with dose-limiting on-target toxicities. A bispecific antibody, which includes a conditional agonist anti-4-1BB portion and a second portion that targets a tumor associated antigen (TAA), has benefit over those that employ an agonist anti-4-1BB portion. The former is believed to be much safer as its anti-4-1BB portion is only active in the presence of the TAA.

Carcinoembryonic antigen-related cell adhesion molecule 5 (CEACAM5), also known as Cluster of Differentiation 66e (CD66e), is a suitable TAA for cancer immunotherapy. CEACAM5 is member of the carcinoembryonic antigen (CEA) gene family. CEACAM5 is a biomarker of many types of malignancies, such as colorectal cancer. Its primary function in the embryonic intestine and colon tumors is adhesion between epithelial cells. It plays a significant role in the inhibition of differentiation and apoptosis in colon cells. High CEACAM5 expression is firmly associated with the CD133-positive colorectal cancer stem cells.

SUMMARY

Provided are bispecific antibodies that target CEACAM5 and 4-1BB. The anti-4-1BB portion includes one or more anti-4-1BB nanobodies which, on their own, do not have agonist activities. In the presence of the CEACAM5 antigen, such as tumor cells that express CEACAM5, the anti-4-1BB antibodies are activated, exerting their immuno-modulating activities.

In accordance with one embodiment of the present disclosure, provided is a bispecific antibody, comprising one or more anti-4-1BB single domain antibodies (VHH) and an anti-CEACAM5 antibody or antigen-binding fragment thereof, wherein the one or more anti-4-1BB single domain antibodies each comprises a complementarity determining region 1 (VHH CDR1), a VHH CDR2 and a VHH CDR3, wherein (a) the VHH CDR1 comprises the amino acid sequence of SEQ ID NO: 21; the VHH CDR2 comprises the amino acid sequence of SEQ ID NO: 22 or 24, and the VHH CDR3 comprises the amino acid sequence of SEQ ID NO: 23; or (b) the VHH CDR1 comprises the amino acid sequence of SEQ ID NO: 21 or 27; the VHH CDR2 comprises the amino acid sequence of SEQ ID NO: 25 or 28, and the VHH CDR3 comprises the amino acid sequence of SEQ ID NO: 26.

In some embodiments, the VHH CDR1 comprises the amino acid sequence of SEQ ID NO:21, the VHH CDR2 comprises the amino acid sequence of SEQ ID NO:22, and the VHH CDR3 comprises the amino acid sequence of SEQ ID NO:23.

In some embodiments, the one or more anti-4-1BB single domain antibodies each comprises an amino acid sequence selected from the group consisting of SEQ ID NO:2-10 and 37-38. In some embodiments, the one or more anti-4-1BB single domain antibodies each comprises the amino acid sequence of SEQ ID NO:37.

In some embodiments, the bispecific antibody further comprises an IgG Fc fragment. In some embodiments, the Fc fragment is N-terminal to two anti-4-1BB single domain antibodies, optionally through a peptide linker. In some embodiments, the Fc fragment is C-terminal to two anti-CEACAM5 fragments.

In some embodiments, the bispecific antibody comprises a full-size IgG anti-CEACAM5 antibody and two anti-4-1BB single domain antibodies fused to the C-terminus of the anti-CEACAM5 antibody. In some embodiments, the anti-CEACAM5 antibody or antigen-binding fragment comprises a VH CDR1 comprising the amino acid sequence of SEQ ID NO:31, a VH CDR2 includes the amino acid sequence of SEQ ID NO:32, a VH CDR3 includes the amino acid sequence of SEQ ID NO:33, a VL CDR1 includes the amino acid sequence of SEQ ID NO:34, a VL CDR2 includes the amino acid sequence of SEQ ID NO:35, and a VL CDR3 includes the amino acid sequence of SEQ ID NO:36.

In some embodiments, the anti-CEACAM5 antibody or antigen-binding fragment comprises a VH comprising the amino acid sequence of SEQ ID NO:29 and a VL comprising the amino acid sequence of SEQ ID NO:30.

Also provided, in one embodiment, is a method of treating cancer in a patient in need thereof, comprising administering to the patient an effective amount of the bispecific antibody of the present disclosure. In some embodiments, the cancer is characterized with expression of CEACAM5.

DETAILED DESCRIPTION

Definitions

Figure 1:
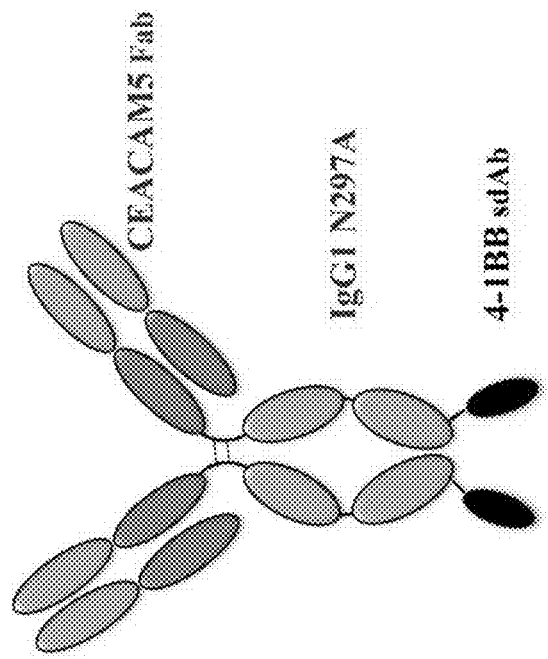
FIG. 1 shows the schematic of anti-CEACAM5-4-1BB bispecific antibody.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Biologically equivalent polynucleotides are those having the above-noted specified percent homology and encoding a polypeptide having the same or similar biological activity.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., salt-bridge) of the reference sequence.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as F(ab')$_2$, F(ab)$_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG$_1$, IgG$_2$, IgG$_3$, IgG$_4$, IgG$_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

CEACAM5-Dependent 4-1BB-Agonistic Bispecific Antibodies

As noted, the leading anti-4-1BB antibodies, such as utomilumab (PF-05082566) and urelumab (BMS-663513), are agonist antibodies. These antibodies are capable of activating 4-1 BB signaling on their own. It is believed that, due to such agnostic nature, these antibodies are associated with dose-limiting on-target toxicities. The instant inventors have developed anti-4-1BB single domain antibodies (sdAb, or nanobodies) that are not independently agonistic. These nanobodies are capable of binding the 4-1BB protein, but cannot activate 4-1BB signaling on their own. When incorporated into a bispecific format with another antibody or antigen-binding fragment that targets a tumor associated antigen (TAA), in the presence of the TAA, the bispecific antibody is then able to activate 4-1BB signaling. Such antibodies are referred to herein as "TAA-dependent 4-1BB-agonistic bispecific antibodies."

CEACAM5-dependent 4-1BB-agonistic bispecific antibodies have been developed in the present disclosure. CEACAM5 is member of the carcinoembryonic antigen (CEA) gene family and is overexpressed in many cancer types, such as colorectal cancer. It plays a significant role in the inhibition of differentiation and apoptosis in cancer cells. The bispecific antibodies tested herein have high binding affinity to both GPRC4D and 4-1BB. In addition, these bispecific antibodies can activate CEACAM5-dependent 4-1BB signaling in a concentration dependent manner.

Figure 13:
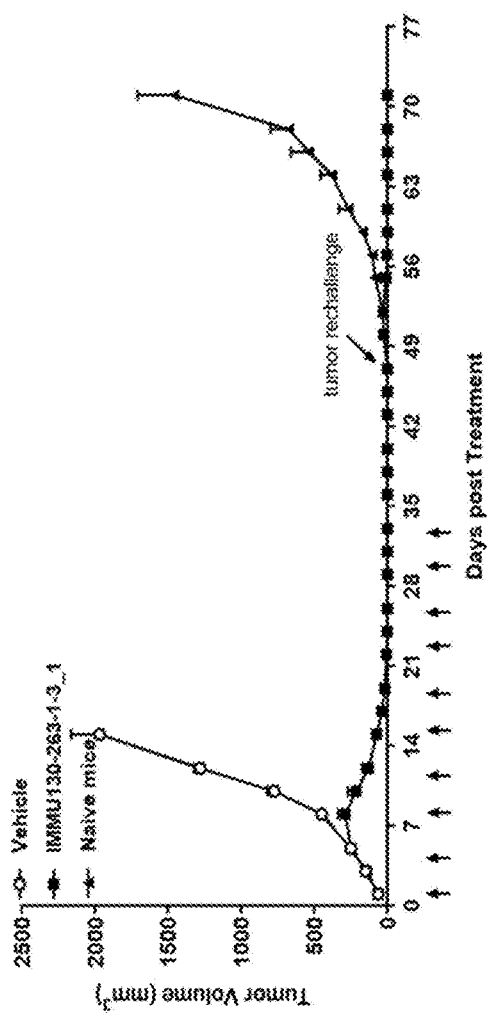
FIG. 13 shows that the bispecific antibody IMMU130-263-1-3_1 exhibited strong anti-tumor efficacy in human 4-1BB transgenic mice tumor model.

In vivo testing showed that treatment with the bispecific antibodies of the present disclosure led to complete tumor regression. Also important, unexpectedly, further tumor re-challenge to the treated animals, without further dosing, did not result in tumor growth (FIG. 13). This means that those treatment with the bispecific antibody induced long-term protective immunological memory.

The format of the bispecific antibodies tested is illustrated in FIG. 1, but it is contemplated that other commonly used formats can also work. In FIG. 1, two anti-4-1BB nanobodies are fused to the C-termini of the Fc fragment of a full-size conventional Fab antibody targeting CEACAM5.

Accordingly, in one embodiment, provided is a bispecific (or multispecific) antibody that includes an anti-4-1BB nanobody of the present disclosure, or an antigen-binding fragment thereof, and a second antibody or antigen-binding fragment having binding specificity to CEACAM5. In some embodiments, a third or fourth specificity is further included.

In one embodiment, the bispecific antibody includes a full-size conventional IgG antibody to CEACAM5 and two anti-4-1BB nanobodies, as illustrated in FIG. 1. In an alternative embodiment, the bispecific antibody includes an anti-4-1BB nanobody that replaces one of the VH-CHI/VL-CL pair of the conventional anti-CEACAM5 antibody. In another embodiment, the bispecific antibody includes two serially-connected (concatenated) anti-4-1BB nanobodies in a single chain that replaces one of the VH-CHI/VL-CL pair of the conventional anti-CEACAM5 antibody.

In another embodiment, the bispecific antibody includes one, two or four anti-4-1BB nanobodies fused to the N-terminus of one or more variable regions of the anti-CEACAM5 antibody. For instance, two anti-4-1BB nanobodies can be fused to the N-termini of the two VH chains. In another example, two anti-4-1BB nanobodies can be fused to the N-termini of the two VL chains. In another example, four anti-4-1BB nanobodies can be fused to the N-termini of the all of the VH/VL chains.

In some embodiments, the bispecific antibody includes the constant regions of human IgG, such as IgG1, IgG2, IgG3 or IgG4. In some embodiments, the constant regions are mutated (e.g., N297A) to prevent post-translational modification. In some embodiments, the constant regions are modified to increase or remove ADCC activity. In some embodiments, the Fc is IgG1 Fc. In some embodiments, the IgG1 Fc has a N297A (Eu numbering) for reduced or eliminated effector functions. In some embodiments, the Fc is an IgG4 Fc. In some embodiments, the Fc has reduced or eliminated binding to the Fc receptors (e.g., FcγRI and FcγRII). In some embodiments, the Fc is an IgG4 Fc with the FALA substitutions (F234A, L235A, EU numbering).

Anti-4-1BB Nanobodies

The present disclosure provides nanobodies, including humanized ones, against the human 4-1BB protein, which can be used in the bispecific antibodies. These antibodies have high binding affinity to 4-1BB and can effectively block the interaction between 4-1BB and its ligand. These antibodies exhibited potent ability to induce 4-1BB-mediated NF-κB activity only in the presence of Fc crosslinking. Therefore, these antibodies are non-agonist antibodies which do not activate 4-1BB signaling on their own. When combined with a second antibody, however, the ensuing bispecific antibody can activate 4-1BB signaling in the presence of the target antigen of the second antibody. In other words, the present nanobodies are particularly suitable for development into bispecific or multispecific antibodies.

Accordingly, in one embodiment of the present disclosure, provided is a single domain antibody or a polypeptide (e.g., a bispecific or multispecific antibody) comprising the single domain antibody, wherein the single domain antibody includes a CDR1, a CDR2 and a CDR3. In some embodiments, the CDR1 includes the amino acid sequence of SEQ ID NO:21, the CDR2 includes the amino acid sequence of SEQ ID NO:22 or 24, and the CDR3 includes the amino acid sequence of SEQ ID NO:23.

In some embodiments, the CDR1 includes the amino acid sequence of SEQ ID NO:21, the CDR2 includes the amino acid sequence of SEQ ID NO:22, and the CDR3 includes the amino acid sequence of SEQ ID NO:23.

In some embodiments, the CDR1, CDR2 and CDR3 include the amino acid sequences of SEQ ID NO:21, 22 and 23, respectively. In some embodiments, the antibody includes the recited CDR1, CDR2 and CDR3 and has at least 80%, 85%, 90%, 95%, 98%, or 99% sequence identity to SEQ ID NO:2. In some embodiments, the antibody includes the recited CDR1, CDR2 and CDR3 and has at least 80%, 85%, 90%, 95%, 98%, or 99% sequence identity to SEQ ID NO:3. In some embodiments, the antibody includes the recited CDR1, CDR2 and CDR3 and has at least 80%, 85%, 90%, 95%, 98%, or 99% sequence identity to SEQ ID NO:4. In some embodiments, the antibody includes the recited CDR1, CDR2 and CDR3 and has at least 80%, 85%, 90%, 95%, 98%, or 99% sequence identity to SEQ ID NO:5. In some embodiments, the antibody includes the recited CDR1, CDR2 and CDR3 and has at least 80%, 85%, 90%, 95%, 98%, or 99% sequence identity to SEQ ID NO:6. In some embodiments, the antibody includes the recited CDR1, CDR2 and CDR3 and has at least 80%, 85%, 90%, 95%, 98%, or 99% sequence identity to SEQ ID NO:7. In some embodiments, the antibody includes the recited CDR1, CDR2 and CDR3 and has at least 80%, 85%, 90%, 95%, 98%, or 99% sequence identity to SEQ ID NO:8. In some embodiments, the antibody includes the recited CDR1, CDR2 and CDR3 and has at least 80%, 85%, 90%, 95%, 98%, or 99% sequence identity to SEQ ID NO:9. In some embodiments, the antibody includes the recited CDR1, CDR2 and CDR3 and has at least 80%, 85%, 90%, 95%, 98%, or 99% sequence identity to SEQ ID NO:10. In some embodiments, the antibody includes the recited CDR1, CDR2 and CDR3 and has at least 80%, 85%, 90%, 95%, 98%, or 99% sequence identity to SEQ ID NO:37. In some embodiments, the antibody includes the recited CDR1, CDR2 and CDR3 and has at least 80%, 85%, 90%, 95%, 98%, or 99% sequence identity to SEQ ID NO:38.

In some embodiments, the CDR1, CDR2 and CDR3 include the amino acid sequences of SEQ ID NO:21, 24 and 23, respectively. In some embodiments, the antibody includes the recited CDR1, CDR2 and CDR3 and has at least 80%, 85%, 90%, 95%, 98%, or 99% sequence identity to SEQ ID NO:1.

In some embodiments, the CDR1 includes the amino acid sequence of SEQ ID NO:21 or 27, the CDR2 includes the amino acid sequence of SEQ ID NO:25 or 28, and the CDR3 includes the amino acid sequence of SEQ ID NO:26.

In some embodiments, the CDR1 includes the amino acid sequence of SEQ ID NO:21, the CDR2 includes the amino acid sequence of SEQ ID NO:25, and the CDR3 includes the amino acid sequence of SEQ ID NO:26.

In some embodiments, the CDR1, CDR2 and CDR3 include the amino acid sequences of SEQ ID NO:21, 25 and 26, respectively. In some embodiments, the antibody includes the recited CDR1, CDR2 and CDR3 and has at least 80%, 85%, 90%, 95%, 98%, or 99% sequence identity to SEQ ID NO:12. In some embodiments, the antibody includes the recited CDR1, CDR2 and CDR3 and has at least 80%, 85%, 90%, 95%, 98%, or 99% sequence identity to SEQ ID NO: 13. In some embodiments, the antibody includes the recited CDR1, CDR2 and CDR3 and has at least 80%, 85%, 90%, 95%, 98%, or 99% sequence identity to SEQ ID NO:14. In some embodiments, the antibody includes the recited CDR1, CDR2 and CDR3 and has at least 80%, 85%, 90%, 95%, 98%, or 99% sequence identity to SEQ ID NO:15. In some embodiments, the antibody includes the recited CDR1, CDR2 and CDR3 and has at least 80%, 85%, 90%, 95%, 98%, or 99% sequence identity to SEQ ID NO: 16. In some embodiments, the antibody includes the recited CDR1, CDR2 and CDR3 and has at least 80%, 85%, 90%, 95%, 98%, or 99% sequence identity to SEQ ID NO:17. In some embodiments, the antibody includes the recited CDR1, CDR2 and CDR3 and has at least 80%, 85%, 90%, 95%, 98%, or 99% sequence identity to SEQ ID NO:18. In some embodiments, the antibody includes the recited CDR1, CDR2 and CDR3 and has at least 80%, 85%, 90%, 95%, 98%, or 99% sequence identity to SEQ ID NO:19. In some embodiments, the antibody includes the recited CDR1, CDR2 and CDR3 and has at least 80%, 85%, 90%, 95%, 98%, or 99% sequence identity to SEQ ID NO:20.

In some embodiments, the CDR1, CDR2 and CDR3 include the amino acid sequences of SEQ ID NO:27, 28 and 26, respectively. In some embodiments, the antibody includes the recited CDR1, CDR2 and CDR3 and has at least 80%, 85%, 90%, 95%, 98%, or 99% sequence identity to SEQ ID NO:11.

In some embodiments, provided is a single domain antibody or a polypeptide (e.g., a bispecific or multispecific antibody) comprising the single domain antibody, wherein the single domain antibody includes the amino acid sequence of SEQ ID NO:1. In some embodiments, provided is a single domain antibody or a polypeptide (e.g., a bispecific or multispecific antibody) comprising the single domain antibody, wherein the single domain antibody includes the amino acid sequence of SEQ ID NO:2. In some embodiments, provided is a single domain antibody or a polypeptide (e.g., a bispecific or multispecific antibody) comprising the single domain antibody, wherein the single domain antibody includes the amino acid sequence of SEQ ID NO:3. In some embodiments, provided is a single domain antibody or a polypeptide (e.g., a bispecific or multispecific antibody) comprising the single domain antibody, wherein the single domain antibody includes the amino acid sequence of SEQ ID NO:4. In some embodiments, provided is a single domain antibody or a polypeptide (e.g., a bispecific or multispecific antibody) comprising the single domain antibody, wherein the single domain antibody includes the amino acid sequence of SEQ ID NO:5.

In some embodiments, provided is a single domain antibody or a polypeptide (e.g., a bispecific or multispecific antibody) comprising the single domain antibody, wherein the single domain antibody includes the amino acid sequence of SEQ ID NO:6. In some embodiments, provided is a single domain antibody or a polypeptide (e.g., a bispecific or multispecific antibody) comprising the single domain antibody, wherein the single domain antibody includes the amino acid sequence of SEQ ID NO:7. In some embodiments, provided is a single domain antibody or a polypeptide (e.g., a bispecific or multispecific antibody) comprising the single domain antibody, wherein the single domain antibody includes the amino acid sequence of SEQ ID NO:8. In some embodiments, provided is a single domain antibody or a polypeptide (e.g., a bispecific or multispecific antibody) comprising the single domain antibody, wherein the single domain antibody includes the amino acid sequence of SEQ ID NO:9. In some embodiments, provided is a single domain antibody or a polypeptide (e.g., a bispecific or multispecific antibody) comprising the single domain antibody, wherein the single domain antibody includes the amino acid sequence of SEQ ID NO:10.

In some embodiments, provided is a single domain antibody or a polypeptide (e.g., a bispecific or multispecific antibody) comprising the single domain antibody, wherein the single domain antibody includes the amino acid sequence of SEQ ID NO:37. In some embodiments, provided is a single domain antibody or a polypeptide (e.g., a bispecific or multispecific antibody) comprising the single domain antibody, wherein the single domain antibody includes the amino acid sequence of SEQ ID NO:38.

Anti-CEACAM5 Antibodies and Fragments

Anti-CEACAM5 antibodies and antigen-binding fragments are also provided, suitable for inclusion in the bispecific/multispecific antibodies of the instant disclosure. In some embodiments, the anti-CEACAM5 antibody or antigen-binding fragment includes a VH and a CL, each including a CDR1, CDR2 and CDR3.

In some embodiments, the VH CDR1 includes the amino acid sequence of SEQ ID NO:31, the VH CDR2 includes the amino acid sequence of SEQ ID NO:32, the VH CDR3 includes the amino acid sequence of SEQ ID NO:33, the VL CDR1 includes the amino acid sequence of SEQ ID NO:34, the VL CDR2 includes the amino acid sequence of SEQ ID NO:35, and the VL CDR3 includes the amino acid sequence of SEQ ID NO:36.

In some embodiments, the VH includes the recited VH CDR sequences and has at least 80%, 85%, 90%, 95%, 98%, or 99% sequence identity to SEQ ID NO:29. In some embodiments, the VL includes the recited VL CDR sequences and has at least 80%, 85%, 90%, 95%, 98%, or 99% sequence identity to SEQ ID NO:30.

In some embodiments, the VH includes the amino acid sequence of SEQ ID NO:29 and the VL includes the amino acid sequence of SEQ ID NO:30.

In some embodiments, the bispecific antibody includes (1) one or more anti-4-1BB nanobodies each having CDR1, CDR2 and CDR3 with the amino acid sequences of SEQ ID NO:21, 22 and 23, respectively, and (2) one or more anti-CEACAM5 antigen-binding fragments each having a VH CDR1 of SEQ ID NO:31, a VH CDR2 of SEQ ID NO:32, a VH CDR3 of SEQ ID NO:33, a VL CDR1 of SEQ ID NO:34, a VL CDR2 of SEQ ID NO:35, and a VL CDR3 of SEQ ID NO:36.

In some embodiments, the bispecific antibody includes (1) one or more anti-4-1BB nanobodies each having the amino acid sequence of SEQ ID NO: 37, and (2) one or more anti-CEACAM5 antigen-binding fragments each having a VH of SEQ ID NO:29, and a VL of SEQ ID NO:30. In some embodiments, the bispecific antibody includes (1) one or more anti-4-1BB nanobodies each having the amino acid sequence of SEQ ID NO: 38, and (2) one or more anti-CEACAM5 antigen-binding fragments each having a VH of SEQ ID NO:29, and a VL of SEQ ID NO:30.

In some embodiments, the bispecific antibody includes a full-size IgG anti-CEACAM5 antibody and two anti-4-1BB nanobodies fused to the C-terminus of the Fc fragment of the anti-CEACAM5 antibody.

Also provided are compositions that include the antibody or the polypeptide and a pharmaceutically acceptable carrier.

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence. In some embodiments, the modified antibody or fragment retains the designate CDR sequences.

In certain embodiments, the antibody comprises an amino acid sequence or one or more moieties not normally associated with an antibody. Exemplary modifications are described in more detail below. For example, an antibody of the disclosure may comprise a flexible linker sequence, or may be modified to add a functional moiety (e.g., PEG, a drug, a toxin, or a label).

Polynucleotides Encoding the Antibodies and Methods of Preparing the Antibodies

The present disclosure also provides isolated polynucleotides or nucleic acid molecules encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

Cancer Treatment

As described herein, the antibodies, bispecific antibodies, polypeptides, variants or derivatives of the present disclosure may be used in certain treatment and diagnostic methods.

The present disclosure is further directed to antibody-based therapies which involve administering the antibodies of the disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein) and nucleic acids or polynucleotides encoding antibodies of the disclosure (including variants and derivatives thereof as described herein).

In some embodiments, provided are methods for treating a cancer in a patient in need thereof. The method, in one embodiment, entails administering to the patient an effective amount of an antibody of the present disclosure. In some embodiments, at least one of the cancer cells (e.g., stromal cells) in the patient over-express a tumor antigen.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, thyroid cancer, endometrial cancer, melanoma, prostate cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma. In some embodiments, the cancer is multiple myeloma.

Compositions

The present disclosure also provides pharmaceutical compositions. Such compositions comprise an effective amount of an antibody, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

EXAMPLES

Example 1: Generation and Humanization of Nanobodies Against Human 4-1BB

This example describes the generations of nanobodies against the human 4-1BB protein.

Llamas were immunized with recombinant ECD of human 4-1BB fused to a human immunoglobulin Fc domain. Llamas whose sera contained sufficient titers of anti-4-1BB antibody were selected for generation of phage libraries. Briefly, lymphocytes were isolated from peripheral blood collected from immunized llamas. The lymphocyte RNA was extracted and cDNA encoding VHH domains was amplified by PCR and used for the construction of M13 phage-display-based nanobody libraries. Several rounds of panning were applied to screen the phage libraries expressing anti-4-1BB nanobodies.

All the positive clones were screened through ELISA and FACS assays prior to sequencing. Based on the sequence diversity, 16 unique clones were selected. The anti-4-1BB nanobodies fused with human IgG1 Fc fragment with N297A mutation at the C-terminus were characterized for their specificity and activity through a series of functional assays including binding, ligand competition and 4-1BB signal activation which resulted in the identification of lead nanobodies for further humanization.

Follow-up studies tested the binding properties of the resulting anti-4-1BB nanobodies to human and cynomolgus 4-1BB proteins by ELISA assay, for their ability to block the binding of 4-1BB to its ligand, and evaluated their functional property in a 4-1BB reporter assay. The results from these studies helped to determine two of them, VV02-1LP-263 and VV02-1SP (1)-73, as lead antibodies, which were subjected to humanization.

The humanization was conducted by CDR grafting and back-mutation strategy. The sequences of the VV02-1LP-263 and VV02-1SP (1)-73 antibodies and their humanized versions are shown in Table. 1.

TABLE 1

Sequences of lead nanobody and humanized versions

| Antibody | Sequence | SEQ ID NO: |
|---|---|---|
| VV02-1LP-263 | EVQLVESGGGLVQPGGSLRLSCAASGFTFSSSAMSWARQTPGKGFEWVSG <u>IYSDGSTYYTDSVKD</u>RFTISRDNAKNTVYL<u>QMNSL</u>KPEDTAVYYCATWGT LRFGVWAEYDHWGQGTQVTVSS | 1 |
| VV02-1LP-263 huNb_1_1 | EVQLLESGGGLVQPGGSLRLSCAASGFTFSSSAMSWARQAPGKGLEWVSG IYS<u>GG</u>STYY<u>T</u>E<u>SVKD</u>RFTISRDN<u>S</u>KNTYLY<u>LQMNSL</u>RAEDTAVYYCA<u>K</u>WGT LRFGVWAEYDHWGQGTLVTVSS | 2 |
| VV02-1LP-263 huNb_1_2 | EVQLLESGGGLVQPGGSLRLSCAASGFTFSSSAMSWARQAPGKGLEWVSG IYSGGSTYYTESVKDRFTISRDNSKNTVYL<u>QMNSL</u>KPEDTAVYYCAT<u>WGT</u> LRFGVWAEYDHWGQGTLVTVSS | 3 |
| VV02-1LP-263 huNb_1_3 | EVQLLESGGGLVQPGGSLRLSCAASGFTFSSSAMSWARQTPGKGFEWVSG IYSGGSTYYTESVKDRFTISRDNSKNTVYL<u>QMNSL</u>KPEDTAVYYCAT<u>WGT</u> LRFGVWAEYDHWGQGTQVTVSS | 4 |
| VV02-1LP-263 huNb_2_1 | EVQLLESGGGLVQPGGSLRLSCAASGFTFSSSAMSWARQAPGKGFEWVSG IYSGGSTYYTESVKDRFTISRDNSKNTLYL<u>QMNSL</u>RAEDTAVYYCA<u>K</u>WGT LRFGVWAEYDHWGQGTLVTVSS | 5 |
| VV02-1LP-263 huNb_2_2 | EVQLVESGGGLVQPGGSLRLSCAASGFTFSSSAMSWARQAPGKGFEWVSG IYSGGSTYYTESVKDRFTISRDNAKNTVYL<u>QMNSL</u>RPEDTAVYYCAT<u>WGT</u> LRFGVWAEYDHWGQGTLVTVSS | 6 |
| VV02-1LP-263 huNb_2_3 | EVQLVESGGGLVQPGGSLRLSCAASGFTFSSSAMSWARQAPGKGFEWVSG IYSGGSTYYTESVKDRFTISRDNAKNTVYL<u>QMNSL</u>KPEDTAVYYCAT<u>WGT</u> LRFGVWAEYDHWGQGTLVTVSS | 7 |
| VV02-1LP-263 huNb_3_1 | QVQLVESGGGLVKPGGSLRLSCAASGFTFSSSAMSWARQAPGKGLEWVSG IYSGGSTYYTESVKDRFTISRDNAKNSLYL<u>QMNSL</u>RAEDTAVYYCA<u>R</u>WGT LRFGVWAEYDHWGQGTLVTVSS | 8 |
| VV02-1LP-263 huNb_3_2 | QVQLVESGGGLVKPGGSLRLSCAASGFTFSSSAMSWARQAPGKGFEWVSG IYSGGSTYYTESVKDRFTISRDNAKNSLYL<u>QMNSL</u>RPEDTAVYYCAT<u>WGT</u> LRFGVWAEYDHWGQGTQVTVSS | 9 |
| VV02-1LP-263 huNb_3_3 | QVQLVESGGGLVQPGGSLRLSCAASGFTFSSSAMSWARQAPGKGFEWVSG IYSGGSTYYTESVKDRFTISRDNAKNSVYL<u>QMNSL</u>KPEDTAVYYCATWGT LRFGVWAEYDHWGQGTQVTVSS | 10 |
| VV02-1SP (1)-73 | EVDLVESGGGLVQPGGSLRLSCAVSGFTFSNSAMSWARQAPGKEFEWVSS IYSDGKTYYVDSVKGRFTISRDNAKNTVYL<u>QMSSL</u>KPEDTAVYYCATWKT LRVGVWDESDYWGQGTQVTVSS | 11 |
| VV02-1SP (1)-73 huNb_1_1 | EVQLLESGGGLVQPGGSLRLSCAASGFTFS<u>S</u>SAMSWARQAPGKGLEWVS<u>S</u> IYS<u>S</u>GKTYYV<u>E</u>SVKGRFTISRDN<u>S</u>KNTLYL<u>QMNSL</u>RAEDTAVYYCA<u>K</u>WKT LRVGVWDESDYWGQGTLVTVSS | 12 |

TABLE 1-continued

Sequences of lead nanobody and humanized versions

| Antibody | Sequence | SEQ ID NO: |
|---|---|---|
| VV02-1SP (1)-73 huNb_1_2 | EVQLLESGGGLVQPGGSLRLSCAASGFTFSSSAMSWARQAPGKELEWVSS IYSSGKTYYVESVKGRFTISRDNAKNTLYLQMSSLRAEDTAVYYCATWKT LRVGVWDESDYWGQGTLVTVSS | 13 |
| VV02-1SP (1)-73 huNb_1_3 | EVDLVESGGGLVQPGGSLRLSCAVSGFTFSSSAMSWARQAPGKEFEWVSS IYSSGKTYYVESVKGRFTISRDNAKNTVYLQMSSLRPEDTAVYYCATWKT LRVGVWDESDYWGQGTLVTVSS | 14 |
| VV02-1SP (1)-73 huNb_2_1 | EVQLVESGGGLIQPGGSLRLSCAASGFTFSSSAMSWARQAPGKGFEWVSS IYSSGKTYYVESVKGRFTISRDNSKNTLYLQMNSLRAEDTAVYYCARWKT LRVGVWDESDYWGQGTLVTVSS | 15 |
| VV02-1SP (1)-73 huNb_2_2 | EVQLVESGGGLIQPGGSLRLSCAASGFTFSSSAMSWARQAPGKEFEWVSS IYSSGKTYYVESVKGRFTISRDNAKNTLYLQMSSLRAEDTAVYYCATWKT LRVGVWDESDYWGQGTQVTVSS | 16 |
| VV02-1SP (1)-73 huNb_2_3 | EVQLVESGGGLVQPGGSLRLSCAVSGFTFSSSAMSWARQAPGKEFEWVSS IYSSGKTYYVESVKGRFTISRDNAKNTVYLQMSSLRPEDTAVYYCATWKT LRVGVWDESDYWGQGTQVTVSS | 17 |
| VV02-1SP (1)-73 huNb_3_1 | EVQLVESGGGLVQPGGSLRLSCAASGFTFSSSAMSWARQAPGKGFEWVAS IYSSGKTYYVESVKGRFTISRDNAKNSLYLQMNSLRAEDTAVYYCARWKT LRVGVWDESDYWGQGTLVTVSS | 18 |
| VV02-1SP (1)-73 huNb_3_2 | EVQLVESGGGLVQPGGSLRLSCAASGFTFSSSAMSWARQAPGKGFEWVSS IYSSGKTYYVESVKGRFTISRDNAKNSLYLQMSSLRAEDTAVYYCATWKT LRVGVWDESDYWGQGTLVTVSS | 19 |
| VV02-1SP (1)-73 huNb_3_3 | EVQLVESGGGLVQPGGSLRLSCAVSGFTFSSSAMSWARQAPGKEFEWVSS IYSSGKTYYVESVKGRFTISRDNAKNSVYLQMSSLRPEDTAVYYCATWKT LRVGVWDESDYWGQGTLVTVSS | 20 |

For VV02-1LP-263, two mutations (D54G and D61E, Kabat numbering) were introduced to CDR2 to improve developability. For VV02-1SP (1)-73, a mutation (N31S, Kabat numbering) and two mutations (D54S and D61E, Kabat numbering) were introduced to the CDR1 and CDR2, respectively, to improve developability. The original and optimized CDR sequences shown in Table 2 below.

TABLE 2

CDRs

| Antibody | CDR1 | SEQ ID NO: | CDR2 | SEQ ID NO: | CDR3 | SEQ ID NO: |
|---|---|---|---|---|---|---|
| VV02-1LP-263 | SSAMS | 21 | GIYSDGSTYYTDSVKD | 24 | WGTLRFGVWAEYDH | 23 |
| VV02-1LP-263 Humanized | SSAMS | 21 | GIYSGGSTYYTESVKD | 22 | WGTLRFGVWAEYDH | 23 |
| VV02-1SP (1)-73 | NSAMS | 27 | SIYSDGKTYYVDSVKG | 28 | WKTLRVGVWDESDY | 26 |
| VV02-1SP (1)-73 Humanized | SSAMS | 21 | SIYSSGKTYYVESVKG | 25 | WKTLRVGVWDESDY | 26 |

To evaluate the antigen binding property in a cell-based setting, the 4-1BB humanized nanobodies were analyzed for their binding to 4-1BB overexpressed on CHO-K1 cells by FACS.

Figure 2:
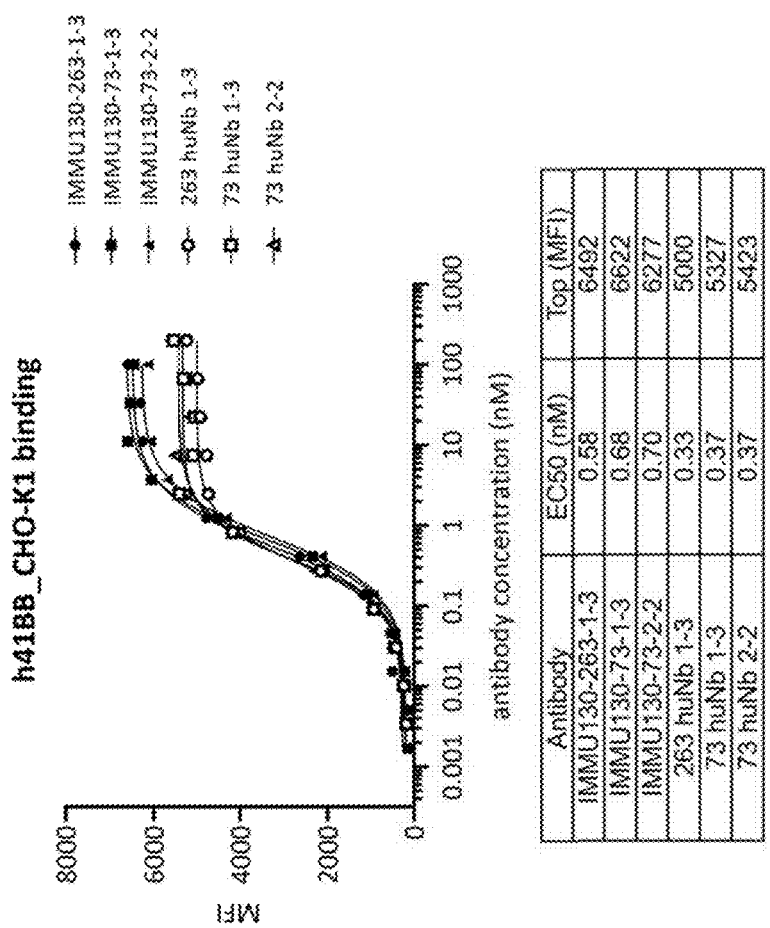
FIG. 2 shows that the anti-41BB humanized nanobodies from parental clones VV02-1LP-263 and VV02-1SP(1)-73 bound to cell surface human 4-1BB in a concentration-dependent manner.

Briefly, CHO-K1 cells overexpressing human 4-1BB or cynomolgus 4-1BB were incubated with the serial diluted anti-4-1BB nanobodies for 30 min at 4° C. Then, the cells were incubated with Alexa Fluor 633-conjugated anti-human Fc secondary antibody. Binding was measured with an Agilent flow cytometer. The results showed that all the tested humanized nanobodies exhibited typical sigmoidal binding behavior against cell surface human 4-1BB and cyno 4-1BB (FIG. 2A-B). The binding $EC_{50}$ are shown in Tables 3-4 accordingly.

TABLE 3

Binding EC$_{50}$ (nM) on cell surface
4-1BB of humanized nanobodies

|  | CHO-K1/hu4-1BB | | CHO-K1/Cyno-41BB | |
| --- | --- | --- | --- | --- |
|  | EC$_{50}$ (nM) | Max (MFI) | EC$_{50}$ (nM) | Max (MFI) |
| VV02-1LP-263_2 | 0.47 | 47120 | 0.64 | 105589 |
| VV02-1LP-263 huNb_1_2 | 0.17 | 23533 | 0.69 | 99611 |
| VV02-1LP-263 huNb_1_3 | 0.11 | 42059 | 0.33 | 133804 |
| VV02-1LP-263 huNb_2_2 | 0.19 | 23409 | 0.64 | 86388 |
| VV02-1LP-263 huNb_2_3 | 0.11 | 39070 | 0.37 | 129678 |
| VV02-1LP-263 huNb_3_2 | 0.14 | 38041 | 0.70 | 128178 |
| VV02-1LP-263 huNb_3_3 | 0.12 | 40328 | 0.70 | 149247 |

TABLE 4

Binding EC$_{50}$ (nM) on cell surface 4-1BB of humanized
nanobodies from parental clone VV02-1SP (1)-73.

|  | CHO-K1/hu4-1BB | |
| --- | --- | --- |
|  | EC50 (nM) | Max (MFI) |
| VV02-1SP (1)-73 huNb_1_1 | — | 233.1 |
| VV02-1SP (1)-73 huNb_1_2 | 0.80 | 5243 |
| VV02-1SP (1)-73 huNb_1_3 | 0.61 | 9809 |
| VV02-1SP (1)-73 huNb_2_2 | 0.37 | 9270 |
| VV02-1SP (1)-73 huNb_2_3 | 0.49 | 9238 |
| VV02-1SP (1)-73 huNb_3_1 | 27.39 | 3700 |
| VV02-1SP (1)-73 huNb_3_2 | 0.52 | 8562 |
| VV02-1SP (1)-73 huNb_3_3 | 0.66 | 9627 |

Example 2: Generation of Anti-CEACAM5-4-1BB Bispecific Antibody

The anti-CEACAM5-4-1BB bispecific antibody was designed in a tetravalent IgG (H)-VHH fusion-type (FIG. 1), in which Fc domain was IgG1 backbone with N297A mutation to disable Fcγ function. The anti-CEACAM5 portion was placed in full IgG part, while the anti-4-1BB nanobody was a VHH placed at the C-terminal side of the Fc fragment via (G$_4$S)$_4$ (SEQ ID NO:39) linker. The sequence of anti-CEACAM5 arm was adapted from Labetuzumab (Immunomedics, or Immu130; Table 1). The sequences of previous identified anti-4-1BB nanobodies used to construct bispecific antibody were shown in Table 5.

TABLE 5

Anti-CEACAM5 Sequences

| Name | Sequence | SEQ ID NO: |
| --- | --- | --- |
| Labetuzumab (Immu130) VH | EVQLVESGGGVVQPGRSLRLSCSASGFDFTTYWM SWVRQAPGKGLEWIGEIHPDSSTINYAPSLKDRF TISRDNAKNTLFLQMDSLRPEDIGVYFCASLYFG FPWFAYWGQGTPVTVSS | 29 |
| Labetuzumab (Immu130) VL | DIQLTQSPSSLSASVGDRVTITCKASQDVGTSVA WYQQKPGKAPKLLIYWTSTRHTGVPSRFSGSGSG TDFTFTISSLQPEDIATYYCQQYSLYRSFGQGTK VEIK | 30 |

TABLE 5A

CDR Sequences

| Name | CDR | Sequence | SEQ ID NO: |
| --- | --- | --- | --- |
| Labetuzumab | CDR-H1 | TYWMS | 31 |
|  | CDR-H2 | EIHPDSSTINYAPSLKD | 32 |
|  | CDR-H3 | LYFGFPWFAY | 33 |
|  | CDR-L1 | KASQDVGTSVA | 34 |
|  | CDR-L2 | WTSTRHT | 35 |
|  | CDR-L3 | QQYSLYRS | 36 |

The resulting bispecific antibodies were produced transiently in CHO-K1 cells and purified by protein A affinity chromatography. The well-qualified bispecific antibodies were applied to in vitro characterization including cell-based 4-1BB binding, CEACAM5 binding and CEACAM5-dependent 4-1BB activation reporter assay.

Cell-Based 4-1BB Binding

Figure 3:
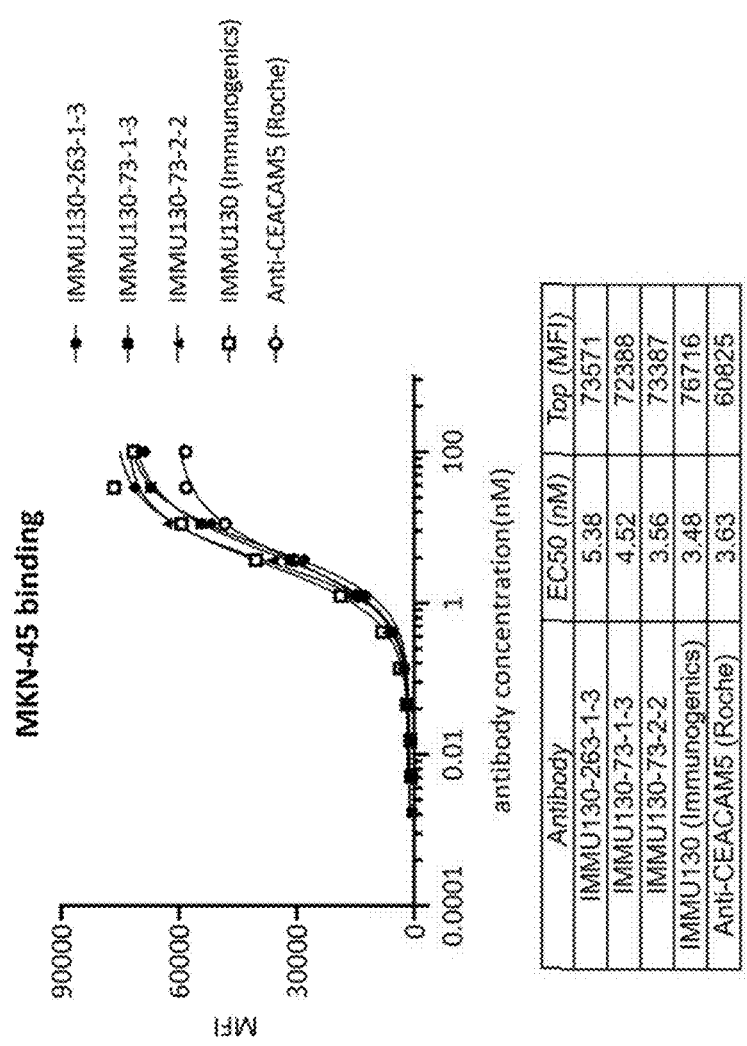
FIG. 3 shows that all the bispecific antibodies bound to human 4-1BB overexpressing CHO-K1 cells in a concentration-dependent manner and all the bispecific antibodies bound to MKN-45 in a concentration-dependent manner.

To evaluate 4-1BB binding activity of bispecific antibodies, CHO-K1 cells overexpressing human 4-1BB were incubated with different concentrations of anti-CEACAM5-4-1BB bispecific antibodies at 4° C. for 30 minutes. Then, the cells were washed twice with FACS buffer and stained with PE conjugated secondary antibody at 4° C. for 30 minutes. After being washed twice with FACS buffer, MFI of PE was analyzed by a NovoCyte flow cytometer. As shown in FIG. 3A, all the bispecific antibodies bound to human 4-1BB overexpressing CHO-K1 cells in a concentration-dependent manner.

Cell-Based CEA CAM5 Binding

To evaluate CEACAM5 binding potency of bispecific antibodies, MKN-45 cells with endogenous expression of CEACAM5 were incubated with different concentrations of anti-CEACAM5-4-1BB bispecific antibodies at 4° C. for 30 minutes. Then, the cells were washed twice with FACS buffer and stained with PE conjugated secondary antibody at 4° C. for 30 minutes. After wash twice with FACS buffer, MFI of PE was analyzed by a NovoCyte flow cytometer. As shown in FIG. 3B, all the bispecific antibodies bound to MKN-45 in a concentration-dependent manner.

CEACAM5-Dependent 4-1BB Activation

Figure 4:
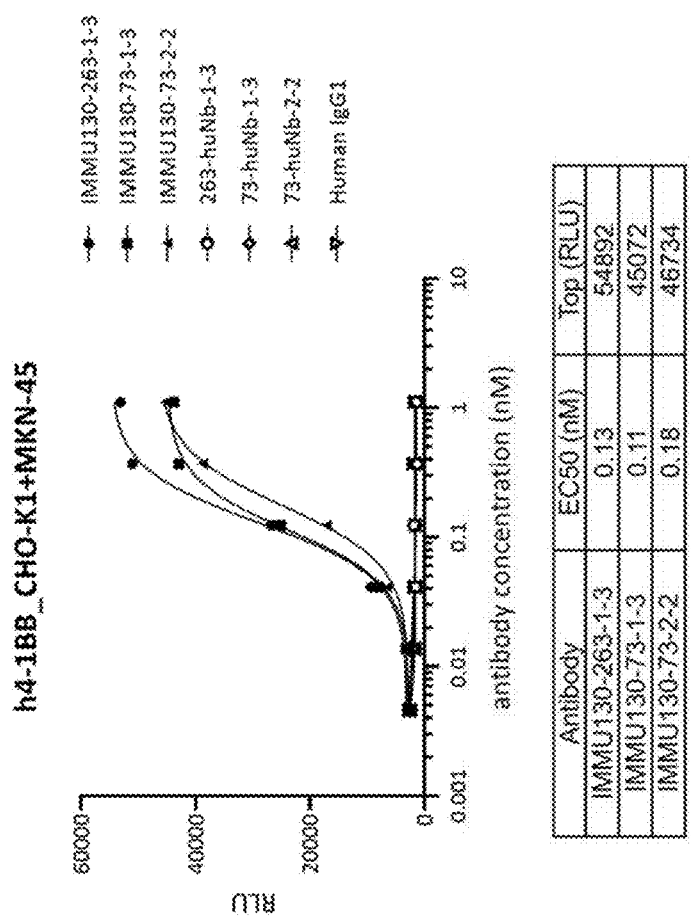
FIG. 4 shows that all the bispecific antibodies activated CEACAM5-dependent 4-1BB signaling in a concentration dependent manner in the presence of MKN45 with endogenous CEACAM5 expression.

To evaluate the ability of anti-CEACAM5-4-1BB bispecific antibody to activate 4-1BB signal, a reporter gene assay was used. In this assay, Jurkat cells engineered to have surface 4-1BB expressing and an NF-κB luciferase reporter construct were used as effector cells. MKN-45 cells were used as target cells. In brief, effector cells at a density of 1E5 cells per well were co-incubated with 1E4 target cells in the presence of 4-fold serially diluted anti-CEACAM5-4-1BB bispecific antibodies at 37° C. in 5% CO$_2$ incubator. After overnight incubation, luminescence was obtained by adding the substrate of luciferase and measured by a microplate reader. As shown in FIG. 4, all the bispecific antibodies activated CEACAM5-dependent 4-1BB signaling in the presence of the target cells MKN-45.

Example 3: Optimization of Anti-CEACAM5-4-1BB Bispecific Antibody

To further increase the developability of candidates, bispecific antibody IMMU130-263-1-3 was selected to be optimized by site-mutation in anti-4-1BB unit. Similar to previous format, optimized anti-4-1BB was placed at the C-terminal side of IgG1 Fc fragment with N297A mutation via G4S linker (SEQ ID NO:39). The optimized sequences of 263 huNb 1-3 were shown in Table 6.

TABLE 6

Optimized 263 huNb 1-3 Sequences

| Name | Sequence | SEQ ID NO: |
|---|---|---|
| 263 huNb-1-3_1 | EVQLVESGGGLVQPGGSLRLSCAASGFTFSS SAMSWARQAPGKGFEWVSGIYSGGSTYYTES VKDRFTISRDNSKNTVYLQMNSLKPEDTAVY YCATWGTLRFGVWAEYDHWGQGTQVTVSS | 37 |
| 263 huNb-1-3_2 | EVQLVESGGGLVQPGGSLRLSCAASGFTFSS SAMSWARQAPGKGFEWVSGIYSGGSTYYTES VKDRFTISRDNAKNTVYLQMNSLKPEDTAVY YCATWGTLRFGVWAEYDHWGQGTLVTVSS | 38 |

The resulting optimized bispecific antibodies were applied to in vitro characterization including cell-based 4-1BB binding, CEACAM5 binding and CEACAM5-dependent 4-1BB activation reporter assay according to the assays described above.

Figure 5:
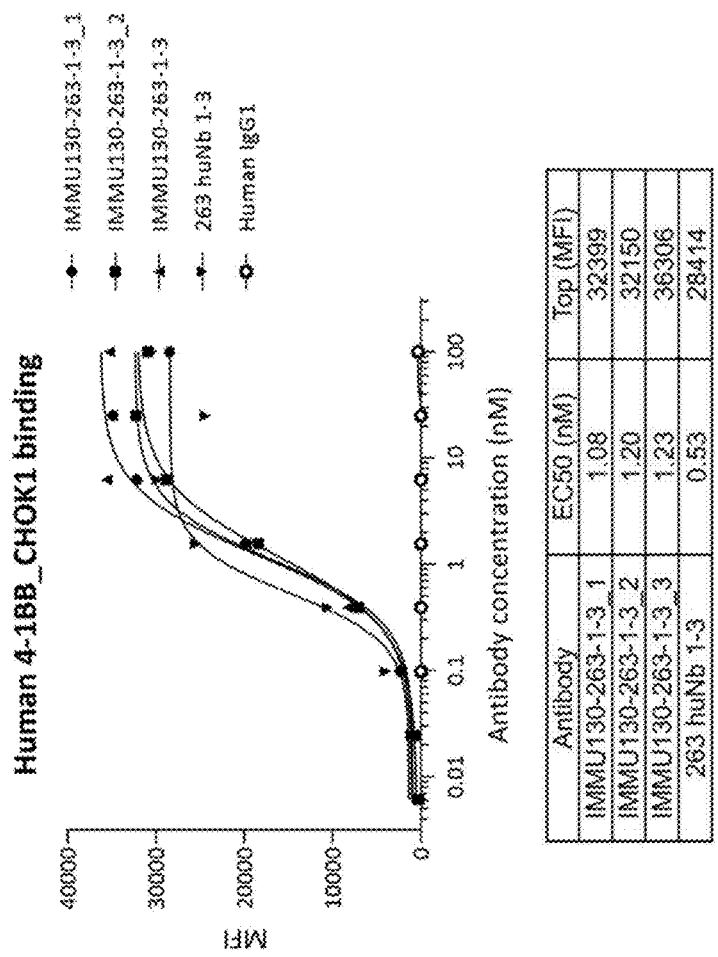
FIG. 5 shows the optimized bispecific antibodies exhibited concentration-dependent binding activity to human 4-1BB overexpressing CHO-K1 cells.
Figure 6:
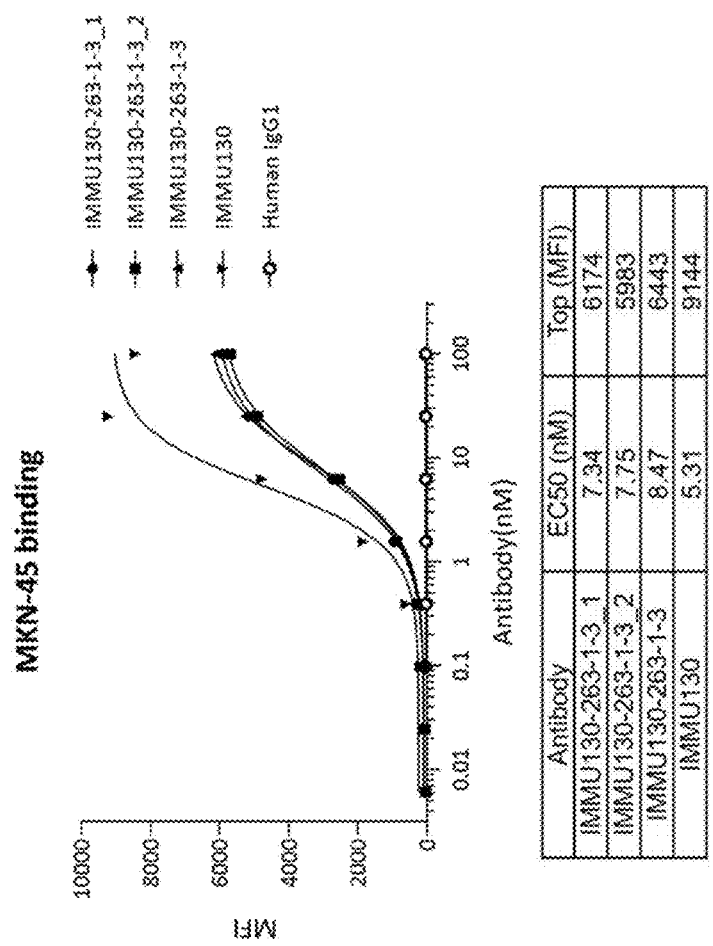
FIG. 6 shows that the optimized bispecific antibodies exhibited similar binding affinity to CEACAM5-bearing MM.1S cells to that of parental bispecific antibody.
Figure 7:
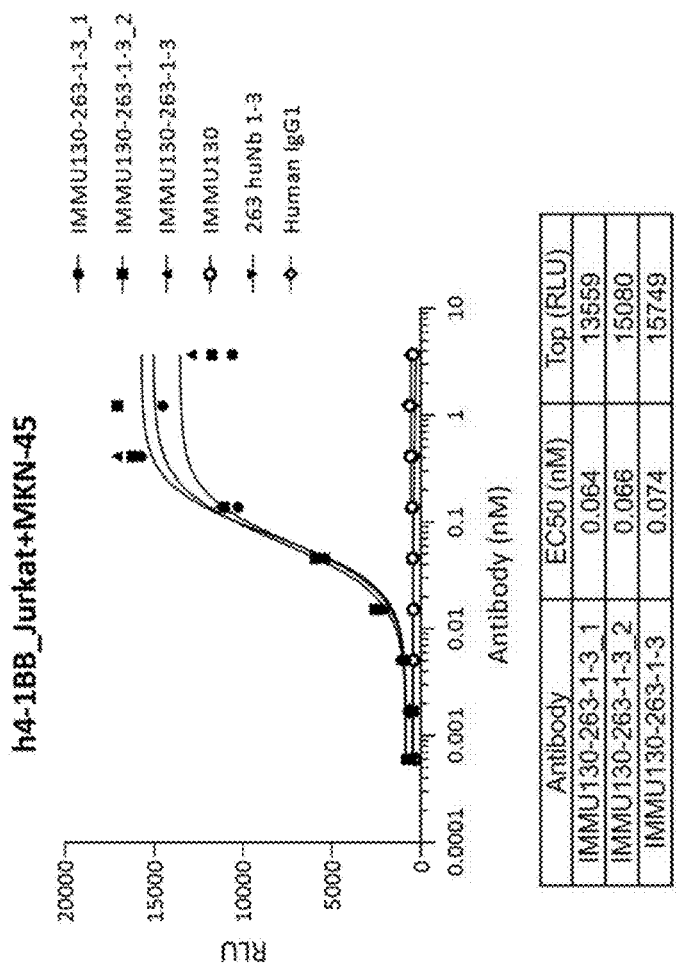
FIG. 7 shows that the optimized bispecific antibodies efficiently induced 4-1BB activation in the presence of target cells MKN-45.

FIG. 5 shows that the optimized bispecific antibodies exhibited comparable binding activity to human 4-1BB overexpressed CHO-K1 cells as the parental antibody. FIG. 6 shows that the optimized bispecific antibodies exhibited similar binding affinity to CEACAM5-bearing MKN-45 cells with the parental bispecific antibody. FIG. 7 shows that the optimized bispecific antibodies efficiently induced 4-1BB activation in the presence of target cells MKN-45.

Example 4: Antigen Binding of the Anti-CEACAM5-4-1BB Bispecific Antibody

This example evaluated the binding activity of the bispecific antibody of IMMU130-263-1-3_1 in Example 3 to CEACAM5 and 4-1BB compared with reference antibodies, using protein-based and cell-based assays.

ELISA Binding to CEACAM5

The anti-CEACAM5-4-1BB bispecific antibody IMMU130-263-1-3_1 was tested for in vitro binding with soluble recombinant CEACAM5 from different species with the parental CEACAM5 antibody Labetuzumab whose sequence was used to construct our bispecific antibody candidate and the reference antibody Cibisatamab as comparators. In a standard ELISA, 100 µL human CEACAM5 protein (Sino-11077-H08H-100UG) at 2 µg/mL diluted in PBS was coated on a microplate at 4° C. overnight, then blocked with 200 pL/well Blocking buffer (1×DPBS with 2% BSA). 5-fold dilution series of antibodies from 200 nM were added and incubated at 25° C. for 60 minutes. Then, the plate was washed twice with ELISA washing buffer (1×DPBS with 0.5% Tween-20) and incubated with peroxidase conjugated secondary antibody at 25° C. for 60 minutes. After washed four times with ELISA washing buffer, the plate was detected by TMB-ELISA Substrate Solution, then stopped by ELISA Stopping Solution and analyzed by a Microplate reader at OD450 nm and OD405 nm.

Figure 8:
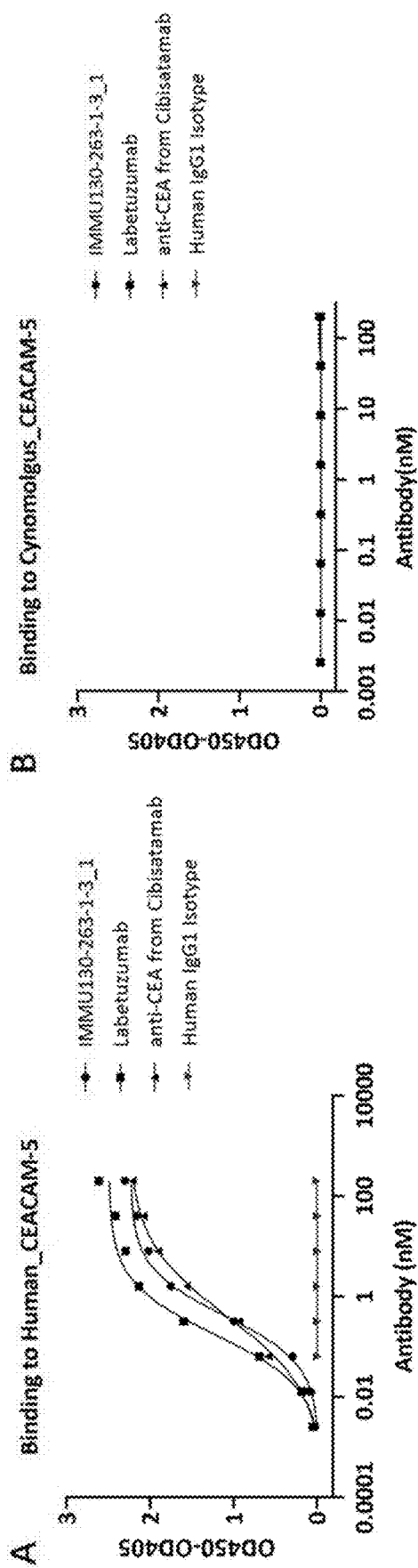
FIG. 8 shows that IMMU130-263-1-3_1 specifically bound to human CEACAM5 protein in a concentration-dependent manner while had no cross-reactivity to cynomolgus CEACAM5.

As shown in FIG. 8, IMMU130-263-1-3_1 specifically bound to human CEACAM5 protein in a concentration-dependent manner. The EC50 was estimated to be 0.41 nM which was comparable to that of the reference antibodies. However, IMMU130-263-1-3_1 showed no cross-reactivity to cynomolgus CEACAM5.

Cell-Based Binding to CEACAM5

Figure 9:
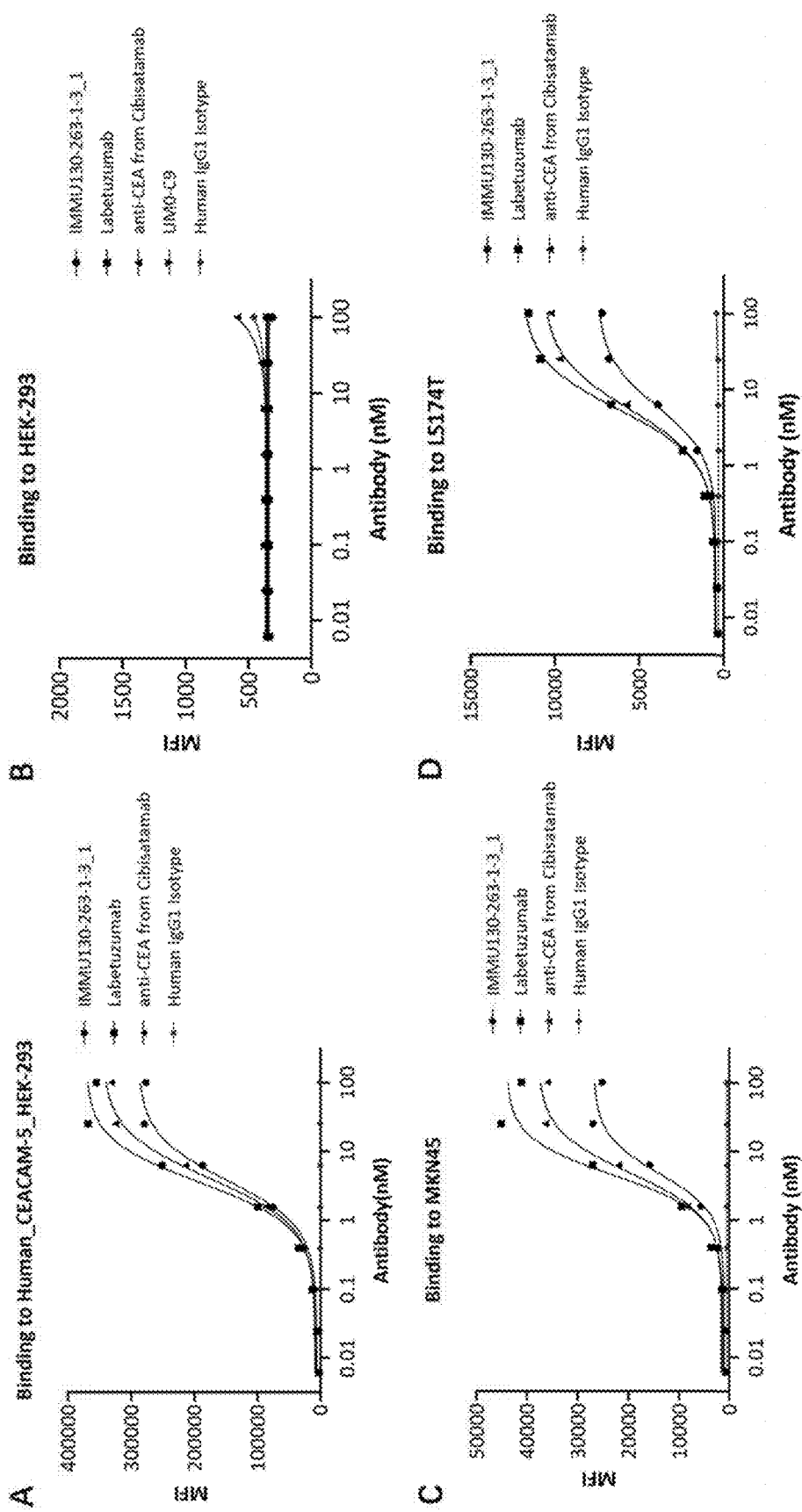
FIG. 9 shows that all the tested antibodies showed typical sigmoidal binding behavior against CEACAM5_HEK293, MKN45 and LS174T cells, while showed no non-specific binding activity to the blank HEK-293 cells.

To evaluate the antigen binding property in a cell-based setting, IMMU130-263-1-3_1 was analyzed for their binding to CEACAM5 overexpressed on HEK293 and tumor cell lines with endogenous CEACAM5 expression by flow cytometry as described in above. The parental CEACAM5 antibody Labetuzumab and the reference antibody Cibisatamab were included in parallel as comparators. As shown in FIG. 9, all the tested antibodies showed typical sigmoidal binding behavior against CEACAM5_HEK293, MKN45 and LS174T cells, while showed no non-specific binding activity to the blank HEK-293 cells. IMMU130-263-1-3_1 efficiently bound to human CEACAM5-expressed HEK-293, MKN45 and LS174T in a concentration-dependent manner with EC50 of 3.78 nM, 4.71 nM and 5.99 nM, respectively.

Cell-Based Binding to 4-1BB

Figure 10:
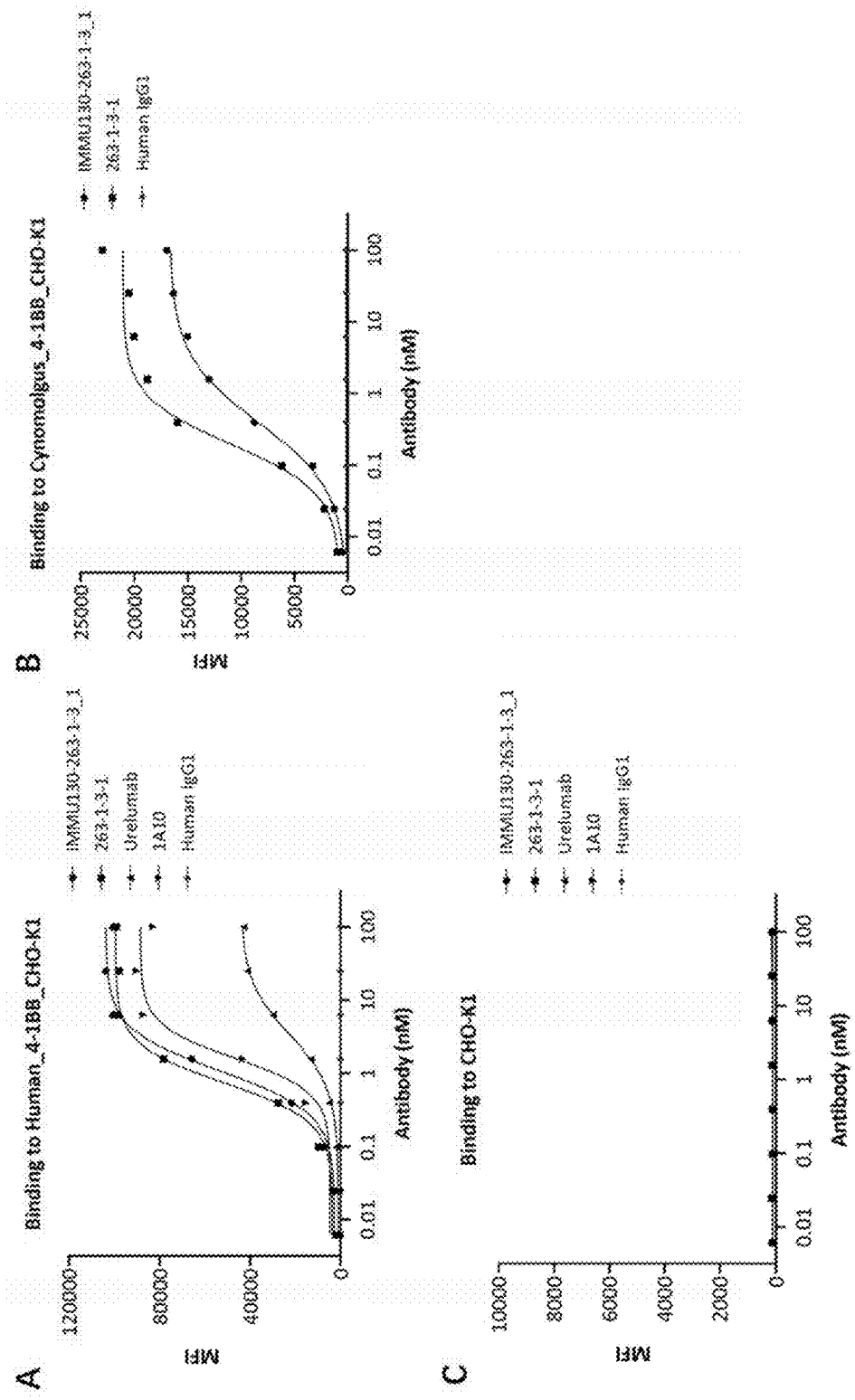
FIG. 10 shows that the bispecific antibody IMMU130-263-1-3_1 efficiently bound to human and cynomolgus 4-1BB over-expressing CHO-K1 cells in a concentration-dependent manner.

The anti-CEACAM5-4-1BB bispecific antibody IMMU130-263-1-3_1 was tested for in vitro binding with 4-1BB expressed on the surface of CHO-K1 cell line with the parental anti-4-1BB antibody 263-1-3-1 as reference. In addition, Urelumab developed by Bristol-Myers Squibb Company and 1A10 developed by ABL Bio, INC. were also compared in parallel with IMMU130-263-1-3_1. As show in FIG. 10, the bispecific antibody efficiently bound to human and cynomolgus 4-1BB over-expressing CHO-K1 cells in a concentration-dependent manner. The mean EC50 of the bispecific antibody was estimated to be 1.07 nM for human 4-1BB and 0.39 nM for cynomolgus 4-1BB. Notably, all the tested antibodies showed no non-specific binding activity to the blank CHO-K1 cells as shown in FIG. 10C.

Example 5: CEACAM5-Dependent 4-1BB Signal Activation in 4-1BB Reporter Assay This example used a classical reporter assay to investigate the ability of the anti-CEACAM5-4-1BB bispecific antibody IMMU130-263-1-3_1 to activate 4-1BB signaling. In this assay, the engineered Jurkat cells which stably express 4-1BB and have an NK-κB luciferase reporter construct integrated into the genome were used as effector cells. HEK-293 cells engineered to overexpress CEACAM5 and tumor cell line MKN45 endogenously expressing CEACAM5 were used as target cells.

Following 4-1BB activation, endogenous NF-κB transcription factors bind to the DNA response elements to induce transcription of the luciferase gene, whose protein product is then quantified by measuring the luminescence signal after adding the substrate. In this study, the effector cells and target cells were co-incubated overnight with different concentrations of IMMU130-263-1-3_1 or reference antibodies at 37° C. in 5% $CO_2$ incubator. Then, the substrate of luciferase was added, and the luminescence intensity was determined by a microplate reader. The parental anti-4-1BB antibody 263-1-3-1 and Urelumab developed by Bristol-Myers Squibb Company were used as reference antibodies.

Figure 11:
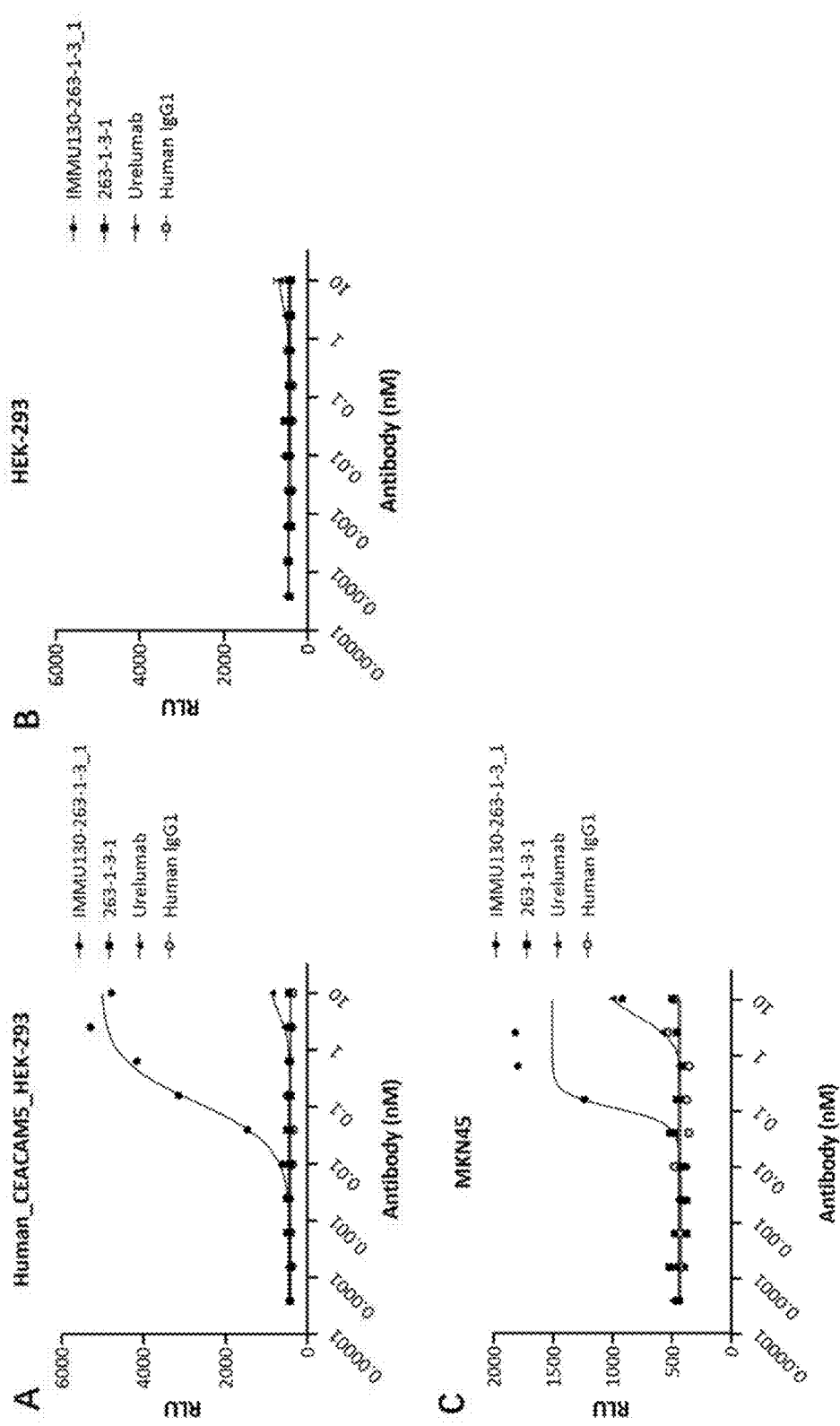
FIG. 11 shows that the bispecific antibody IMMU130-263-1-3_1 induced significant 4-1BB activation in the presence of target cells with CEACAM expression.

As shown in FIG. 11, the bispecific antibody IMMU130-263-1-3_1 induced significant 4-1BB activation in the presence of target cells with CEACAM expression. The $EC_{50}$ of IMMU130-263-1-3_1 was estimated to be 0.12 nM with human CEACAM5_HEK-293 as target cells and 0.11 nM with MKN45 as target cells. Notably, IMMU130-263-1-3_1 failed to activate 4-1BB signaling in the presence of target cells that did not express CEACAM5, indicating that IMMU130-263-1-3_1-mediated 4-1BB activation was dependent on CEACAM5 engagement.

Example 6: CEACAM5-Dependent Primary T Cell Activation

Figure 12:
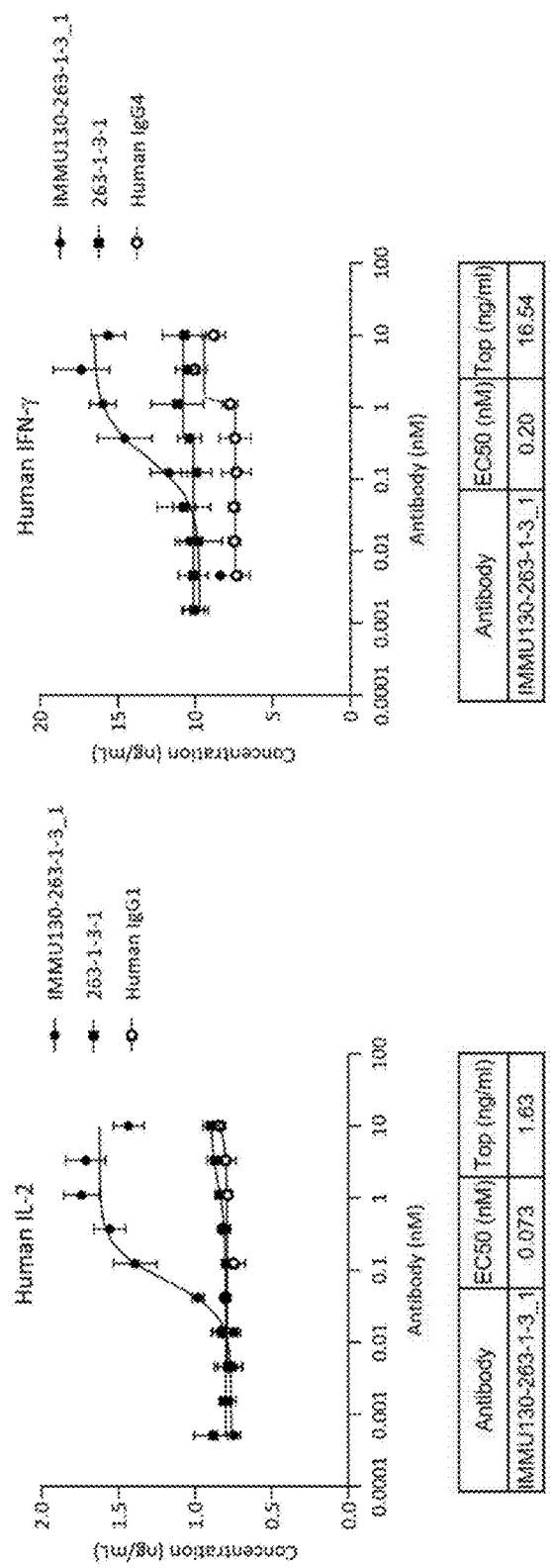
FIG. 12 shows that the bispecific antibody IMMU130-263-1-3_1 induced significant IL-2 and IFN-γ production by primary PBMCs in the presence of target cells overexpressing CEACAM5.

To test the ability of anti-CEACAM5-4-1BB bispecific antibody IMMU130-263-1-3_1 to activate human T cells, human PBMCs (4E5 cells per well) were co-cultured with HEK-293 cells overexpressing CEACAM5 (2E4 cells per well) in the presence of human anti-CD3 antibody (OKT3 at 0.25 μg/mL) and serially diluted bispecific antibody. The level of IL-2 in the culture supernatant was determined by Human IL-2 ELISA KIT (CAT #Mabtech-3445-1H-20) after 24 hours incubation. Meanwhile, the level of IFN-γ was determined by Human IFN-γ ELISA KIT (CAT #Mabtech-3420-1H-20) after 48 hours incubation. As shown in FIG. 12, as compared with the parental 4-1BB antibody, CEACAM5-4-1BB bispecific antibody induced significant cytokines production by primary PBMCs. The $EC_{50}$ for IMMU130-263-1-3_1 was estimated to be 0.073 nM for IL-2 and 0.20 nM for IFN-γ.

Example 7: In Vivo Tumor Growth Inhibition by Bispecific Antibodies

To evaluate anti-tumor efficacy of the anti-CEACAM5-4-1BB bispecific antibody IMMU130-263-1-3_1, a syngeneic mouse tumor model using human 4-1BB transgenic mice inoculated with MC38 cells ectopically expressing human CEACAM5 was employed. Humanized-4-1BB mice were subcutaneously implanted with $1 \times 10^6$ hCEACAM5-MC38 cells. When the average tumor volume grew to 65 mm³, tumor-bearing mice were randomized into two groups (N=6/group) and were intraperitoneally administered vehicle (PBS) and IMMU130-263-1-3_1, respectively. Antibody was given twice a week. Tumor volume was monitored by caliper measurement three times per week for the duration of the experiment.

As shown in FIG. 13, injection of IMMU130-263-1-3_1 led to significant tumor inhibition and five among six mice in the treated group were tumor free by around one month post treatment initiation. When rechallenged with a second dose of the same tumor cells, these five tumor-free mice were resistant to tumor re-challenge and were deemed tumor free while the tumor cells continued to grow in naïve mice, suggesting that the anti-CEACAM5-4-1BB bispecific antibody IMMU130-263-1-3_1 exhibited strong anti-tumor efficacy and induced long-term protective immunological memory.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

What is claimed is:

1. A bispecific antibody, comprising one or more anti-4-1BB single domain antibodies (VHH) and an anti-CEACAM5 antibody or antigen-binding fragment thereof, wherein the one or more anti-4-1BB single domain antibodies each comprises a complementarity determining region 1 (VHH CDR1), a VHH CDR2 and a VHH CDR3, wherein
   (a) the VHH CDR1 comprises the amino acid sequence of SEQ ID NO: 21; the VHH CDR2 comprises the amino acid sequence of SEQ ID NO: 22 or 24, and the VHH CDR3 comprises the amino acid sequence of SEQ ID NO: 23; or
   (b) the VHH CDR1 comprises the amino acid sequence of SEQ ID NO: 21 or 27; the VHH CDR2 comprises the amino acid sequence of SEQ ID NO: 25 or 28, and the VHH CDR3 comprises the amino acid sequence of SEQ ID NO: 26,
   wherein the anti-CEACAM5 antibody or antigen-binding fragment thereof comprises a VH CDR1 comprising the amino acid sequence of SEQ ID NO:31, a VH CDR2 comprising the amino acid sequence of SEQ ID NO:32, a VH CDR3 comprising the amino acid sequence of SEQ ID NO:33, a VL CDR1 comprising the amino acid sequence of SEQ ID NO:34, a VL CDR2 comprising the amino acid sequence of SEQ ID NO:35, and a VL CDR3 comprising the amino acid sequence of SEQ ID NO:36.

2. The bispecific antibody of claim 1, wherein the VHH CDR1 comprises the amino acid sequence of SEQ ID NO:21, the VHH CDR2 comprises the amino acid sequence of SEQ ID NO:22, and the VHH CDR3 comprises the amino acid sequence of SEQ ID NO:23.

3. The bispecific antibody of claim 2, wherein the one or more anti-4-1BB single domain antibodies each comprises an amino acid sequence selected from the group consisting of SEQ ID NO:2-10 and 37-38.

4. The bispecific antibody of claim 2, wherein the one or more anti-4-1BB single domain antibodies each comprises the amino acid sequence of SEQ ID NO:37.

5. The bispecific antibody of claim 1, further comprising an IgG Fc fragment.

6. The bispecific antibody of claim 5, wherein the Fc fragment is N-terminal to two anti-4-1BB single domain antibodies.

7. The bispecific antibody of claim 5, wherein the Fc fragment is C-terminal to two anti-CEACAM5 fragments.

8. The bispecific antibody of claim 1, which comprises an anti-CEACAM5 antibody and two anti-4-1BB single domain antibodies, wherein the anti-CEACAM5 antibody comprises two anti-CEACAM5 Fabs and an IgG Fc fragment that is C-terminal to the two anti-CEACAM5 Fabs, and the two anti-4-1BB single domain antibodies are fused to the C-terminus of the IgG Fc fragment.

9. The bispecific antibody of claim 1, wherein the anti-CEACAM5 antibody or antigen-binding fragment comprises a VH comprising the amino acid sequence of SEQ ID NO:29 and a VL comprising the amino acid sequence of SEQ ID NO:30.

10. One or more polynucleotides encoding the bispecific antibody of claim 1.

11. A cell comprising the polynucleotide of claim 10.

12. A composition comprising the bispecific antibody of claim 1 and a pharmaceutically acceptable carrier.

13. A method of treating cancer in a patient in need thereof, comprising administering to the patient an effective amount of the bispecific antibody of claim 1.

14. The method of claim 13, wherein the cancer is characterized with expression of CEACAM5.

15. A bispecific antibody, comprising one or more anti-4-1BB single domain antibodies (VHH) and an anti-CEACAM5 antibody or antigen-binding fragment thereof, wherein the one or more anti-4-1BB single domain antibodies each comprises a complementarity determining region 1 (VHH CDR1), a VHH CDR2 and a VHH CDR3, wherein
   (a) the VHH CDR1 comprises the amino acid sequence of SEQ ID NO: 21; the VHH CDR2 comprises the amino acid sequence of SEQ ID NO: 22 or 24, and the VHH CDR3 comprises the amino acid sequence of SEQ ID NO: 23; or
   (b) the VHH CDR1 comprises the amino acid sequence of SEQ ID NO: 21 or 27; the VHH CDR2 comprises the amino acid sequence of SEQ ID NO: 25 or 28, and the VHH CDR3 comprises the amino acid sequence of SEQ ID NO: 26,
   wherein the bispecific antibody further comprises an IgG Fc fragment.

16. The bispecific antibody of claim 15, wherein the Fc fragment is N-terminal to two anti-4-1BB single domain antibodies.

17. The bispecific antibody of claim 15, wherein the Fc fragment is C-terminal to two anti-CEACAM5 fragments.

18. A bispecific antibody, comprising one or more anti-4-1BB single domain antibodies (VHH) and an anti-CEACAM5 antibody or antigen-binding fragment thereof, wherein the one or more anti-4-1BB single domain antibodies each comprises the amino acid sequence of SEQ ID NO:37.

* * * * *